(12) United States Patent
Ramesh et al.

(10) Patent No.: US 7,902,185 B2
(45) Date of Patent: Mar. 8, 2011

(54) TREATMENT OF NEURODEGENERATIVE DISEASES USING PROTEASOME MODULATORS

(75) Inventors: Tennore M. Ramesh, Westwood, MA (US); Sean Scott, San Francisco, CA (US)

(73) Assignee: ALS Therapy Development Foundation, Inc., Cambridge, MA (US)

( * ) Notice: Subject to any disclaimer, the term of this patent is extended or adjusted under 35 U.S.C. 154(b) by 1333 days.

(21) Appl. No.: 10/453,912

(22) Filed: Jun. 3, 2003

(65) Prior Publication Data
US 2004/0138153 A1    Jul. 15, 2004

Related U.S. Application Data

(60) Provisional application No. 60/385,489, filed on Jun. 3, 2002, provisional application No. 60/385,625, filed on Jun. 3, 2002.

(51) Int. Cl.
*A01N 43/62* (2006.01)
*A01N 43/04* (2006.01)
*A61K 31/55* (2006.01)
*A61K 31/70* (2006.01)

(52) U.S. Cl. .......................... 514/220; 514/43
(58) Field of Classification Search .................... 514/43, 514/220
See application file for complete search history.

(56) References Cited

U.S. PATENT DOCUMENTS

| | | | |
|---|---|---|---|
| 5,734,054 A | | 3/1998 | Dolle, III et al. |
| 5,843,715 A | * | 12/1998 | Bandman et al. ............ 435/69.1 |
| 2003/0232349 A1 | * | 12/2003 | Delegeane et al. ............... 435/6 |

FOREIGN PATENT DOCUMENTS
WO    WO 03/043616 A2    5/2003

OTHER PUBLICATIONS

Kelly et al. ("Proteasome Modulation by Ritonavir Extends the Life of the SOD1 G93A Mouse Model of Amyotrophic Lateral Sclerosis", Database Accession No. 2003:327040 XP002255235 Abtract, of record).*
Hosseini, Hassan et al. "Protection Against Experimental Autoimmune Encephalomyelitis By A Proteasome Modulator" Journal of Neuroimmunotogy, vol. 118, pp. 233-244 (2001).
Qunxing Ding and Keller, Jeffrey N. "Proteasomes And Proteasome Inhibition In The Central Nervous System" Free Radical Biology & Medicine, vol. 31, No. 5, pp. 574-584 (2001).
DeMartino, George N. and Slaughter, Clive A. "The Proteasome, A Novel Protease Regulated by Multiple Mechanisms", The Journal of Biological Chemistry, vol. 274, No. 32, pp. 22123-22126 (1999).
Andre, Patrice et al. "An Inhibitor of HIV-1 Protease Modulates Proteasome Activity, Antigen Presentation, And T Cell Responses", Proc. Natl. Acad. Sci, USA, vol. 95, pp. 13120-13124 (1998).
Kelly, N et al. "Proteasome Modulation By Ritonavir Extends The Life of The SOD1 G93A Mouse Model of Amyotrophic Lateral Sclerosis", Database Accession No. 2003:327040 XP002255235 Abstract.

* cited by examiner

*Primary Examiner* — Yong S Chong
(74) *Attorney, Agent, or Firm* — Thomas J. Engellenner; Nutter McClennen & Fish LLP

(57) ABSTRACT

Methods for modulating proteasome activity in a subject is provided. Proteasome activity is modulated by administering a therapeutically effective amount of proteasome modulating pharmacological agent to a subject. In a preferred embodiment, the proteasome modulating pharmacological agent is a protease inhibitor. In another aspect, a screening assay for detecting and identifying proteasome modulating pharmacological agents to modulate proteasome activity in a subject is also provided.

12 Claims, 14 Drawing Sheets

Figure 1: Expression of LMP-7, the inducible proteasomal subunit in N2A neuroblastoma cell lines expressing SOD1 mutation.

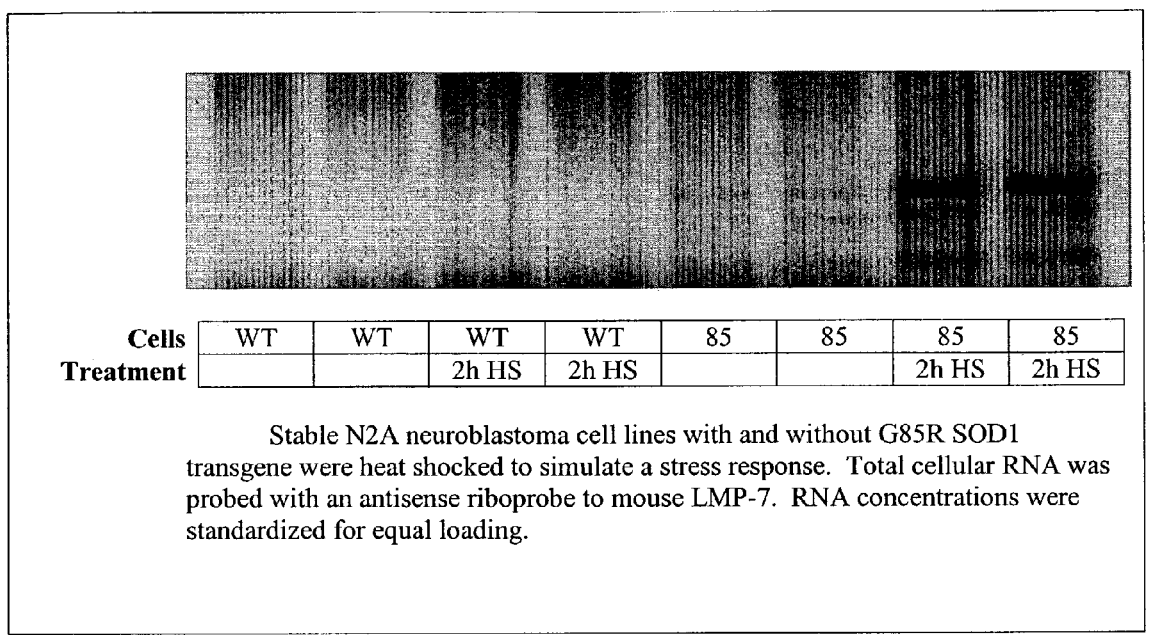

Stable N2A neuroblastoma cell lines with and without G85R SOD1 transgene were heat shocked to simulate a stress response. Total cellular RNA was probed with an antisense riboprobe to mouse LMP-7. RNA concentrations were standardized for equal loading.

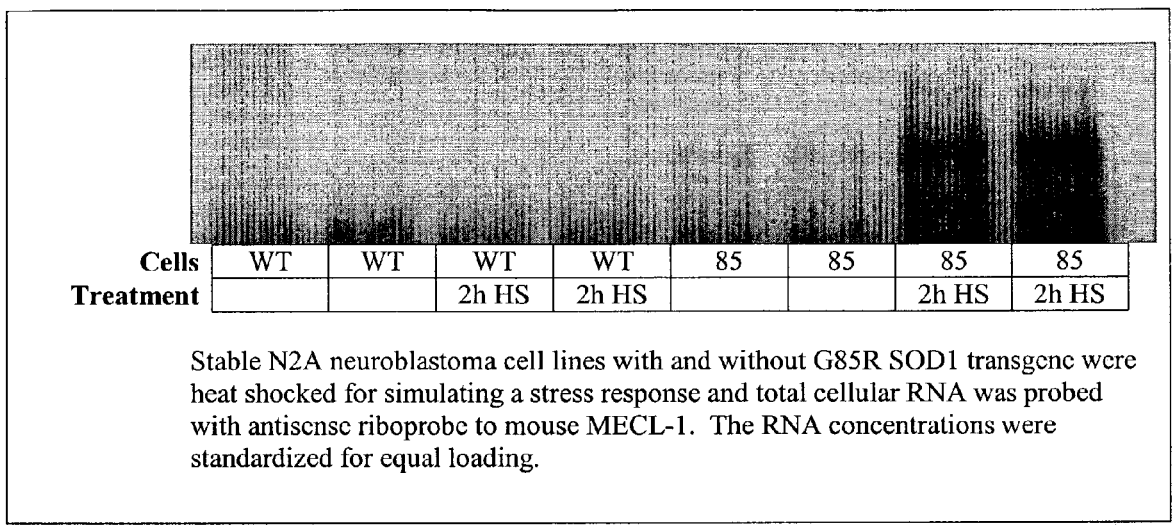

Figure 2: Expression of MECL-1, the inducible proteasomal subunit in N2A neuroblastoma cell lines expressing SOD1 mutation.

Stable N2A neuroblastoma cell lines with and without G85R SOD1 transgene were heat shocked for simulating a stress response and total cellular RNA was probed with antisense riboprobe to mouse MECL-1. The RNA concentrations were standardized for equal loading.

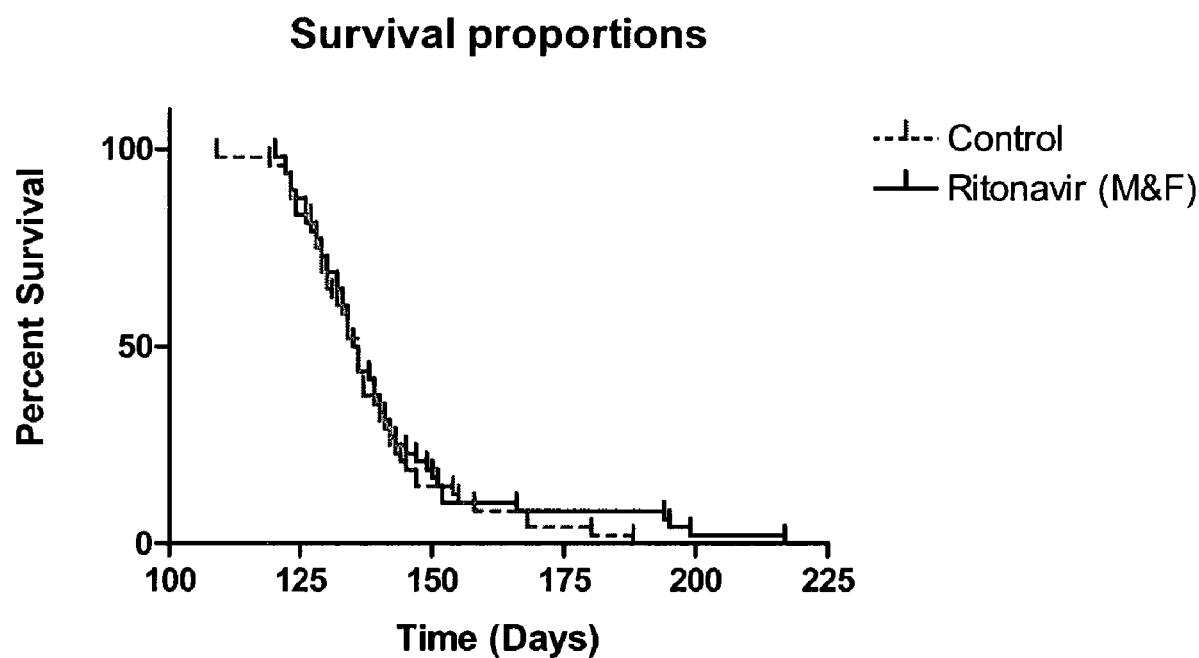
Figure 3: Combined Males and females: Ritonavir I/P @50 mg/Kg.

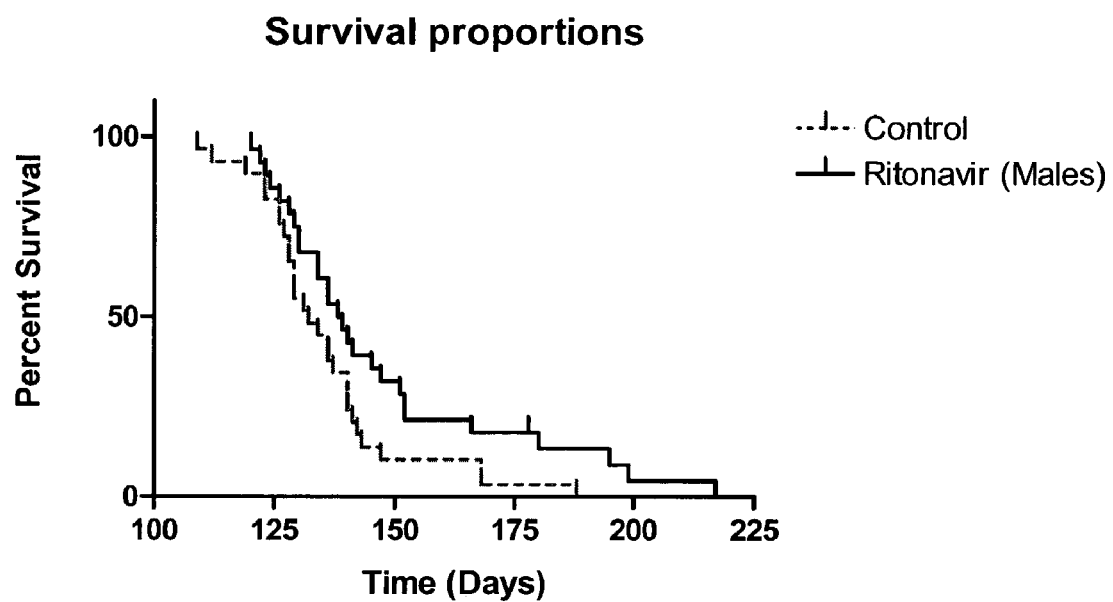
Figure 4: Males: Ritonavir I/P @50 mg/Kg.
Hazard ratio: 0.57, p=0.06 (Cox proportional hazard analysis with frailty term as litter)

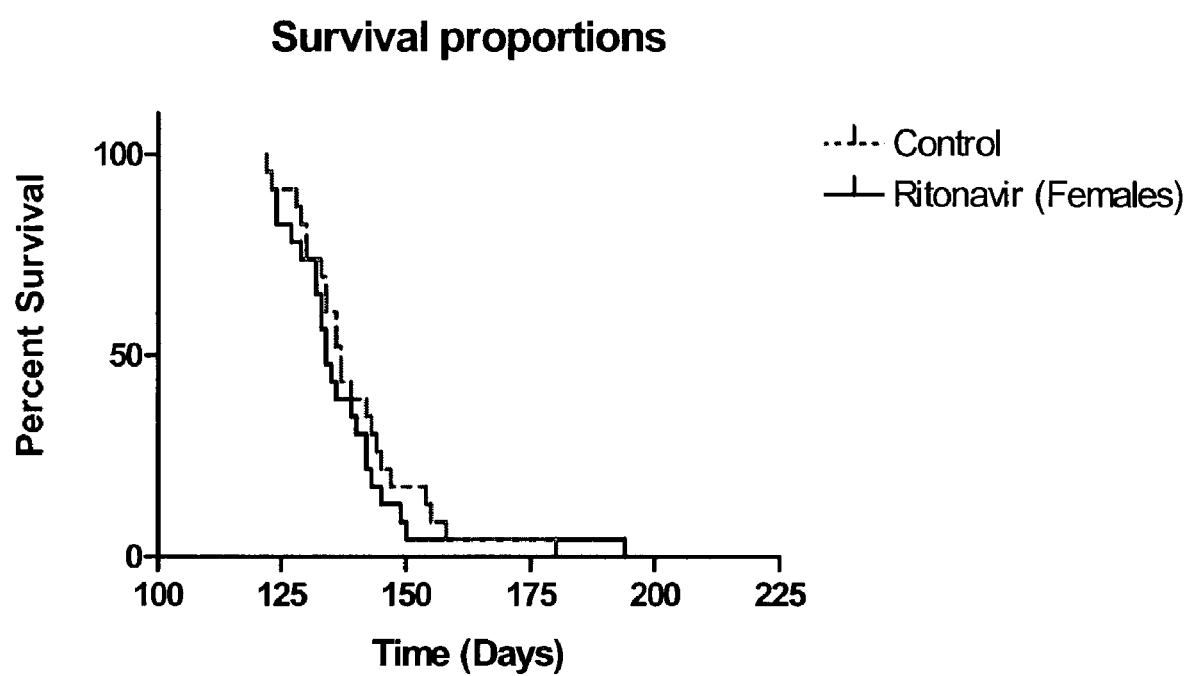
Figure 5: Females: Ritonavir I/P @50 mg/Kg.

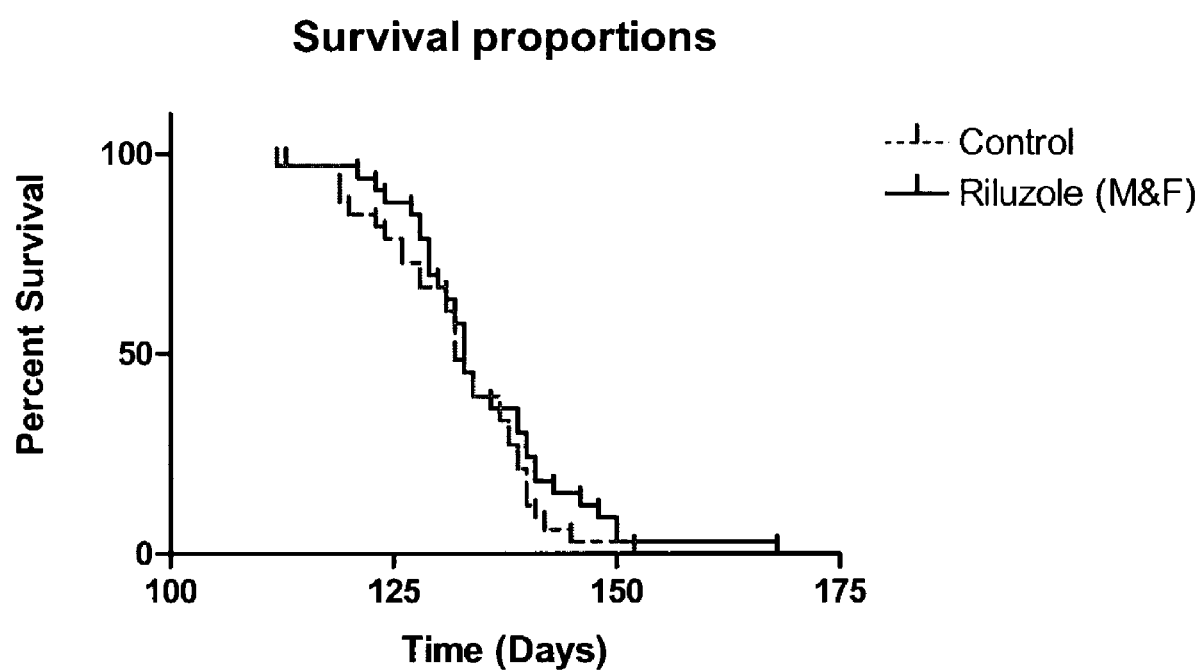
Figure 6: Combined Males and females: Oral Riluzole @20 mg/Kg.

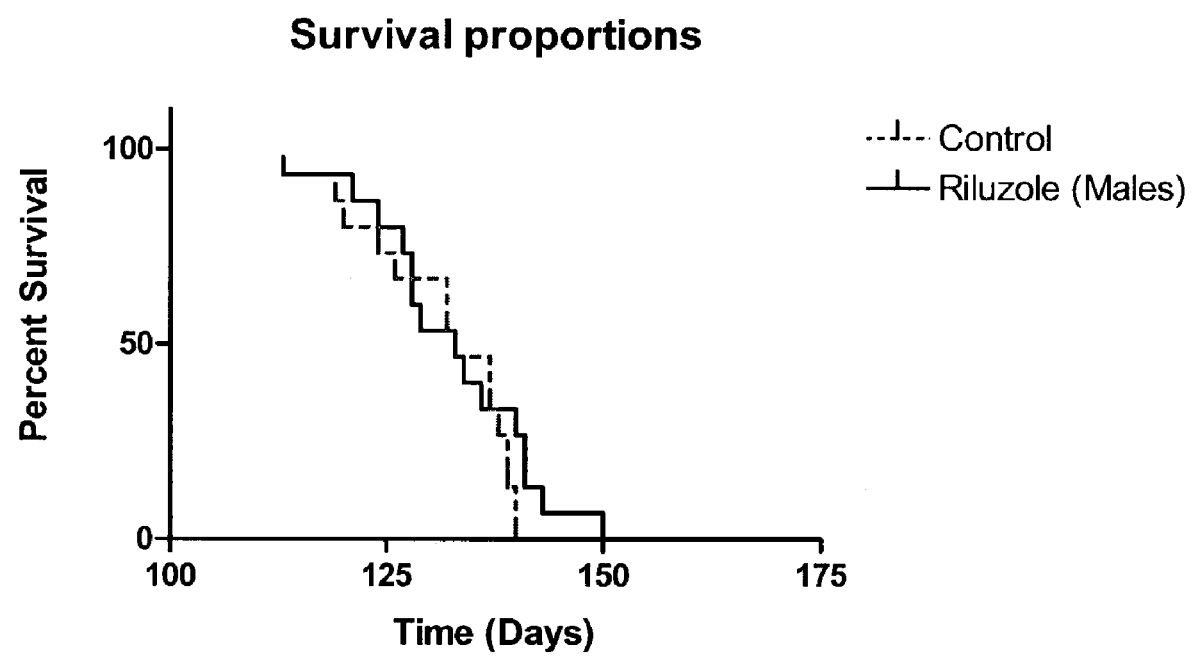
Figure 7: Combined Males: Oral Riluzole @20 mg/Kg.

Figure 8: Combined Females: Oral Riluzole @20 mg/Kg.
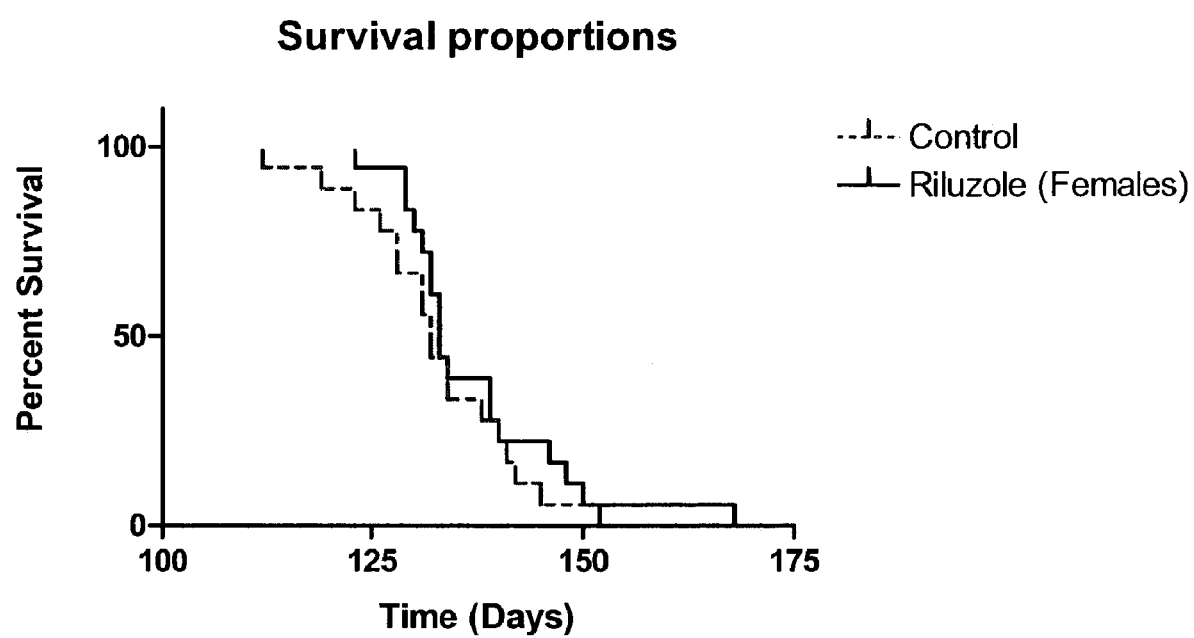

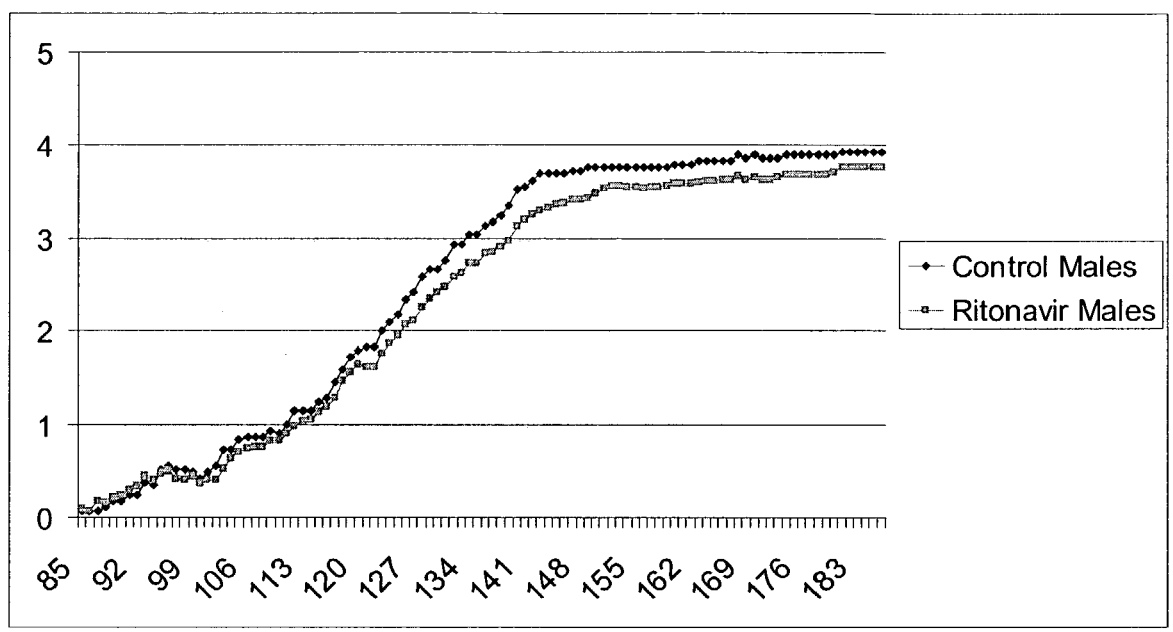
Figure 9: Neuroscore: Combined males: Ritonavir I/P @50 mg/Kg.

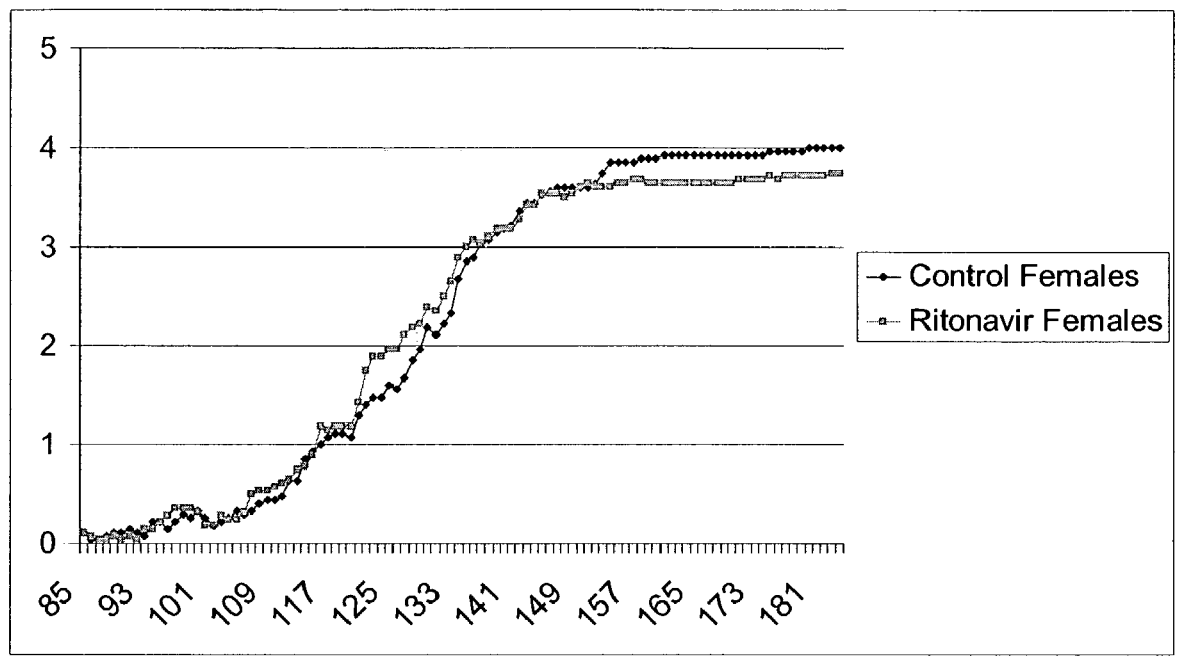
Figure 10: Neuroscore: Combined Females: Ritonavir I/P @50 mg/Kg.

Figure 11: Neuroscore: Combined Males and Females: Ritonavir I/P @50 mg/Kg
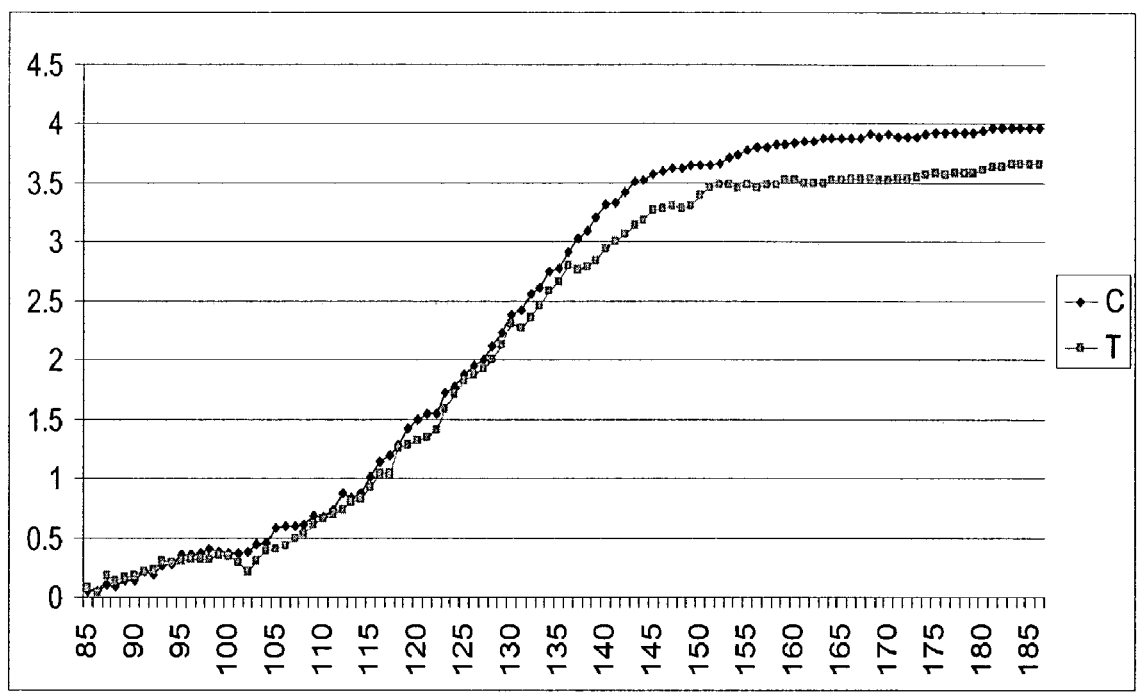

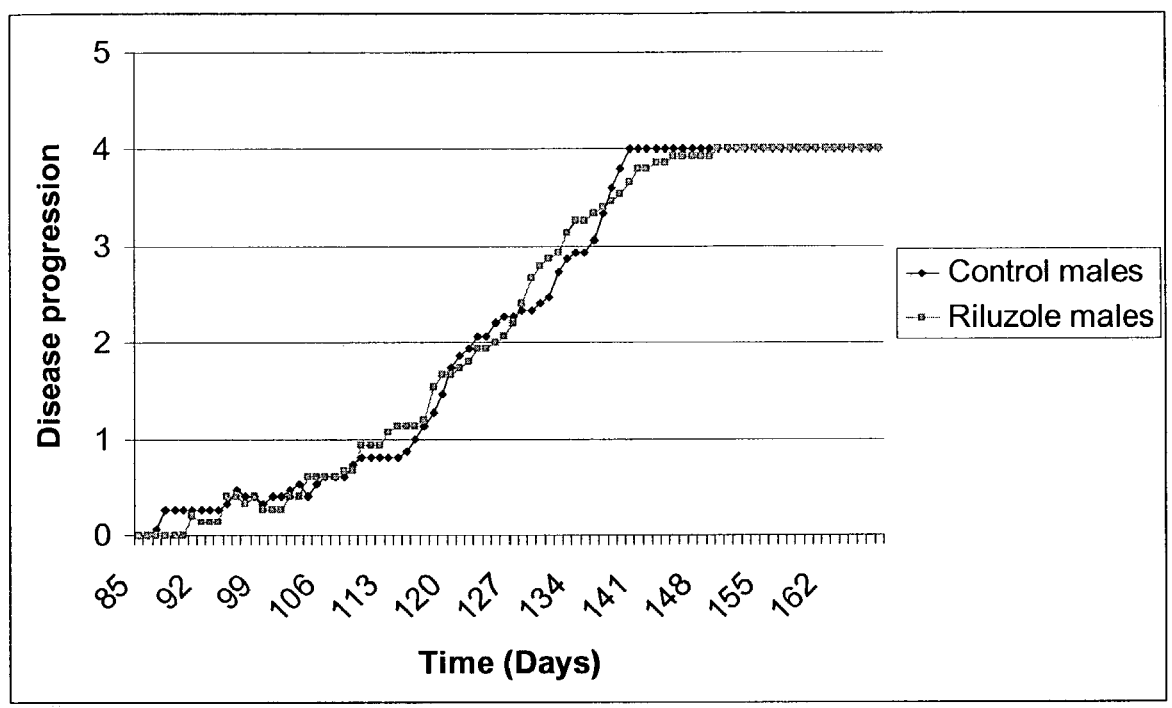
Figure 12: Neuroscore: Combined Males: Riluzole @20 mg/Kg.

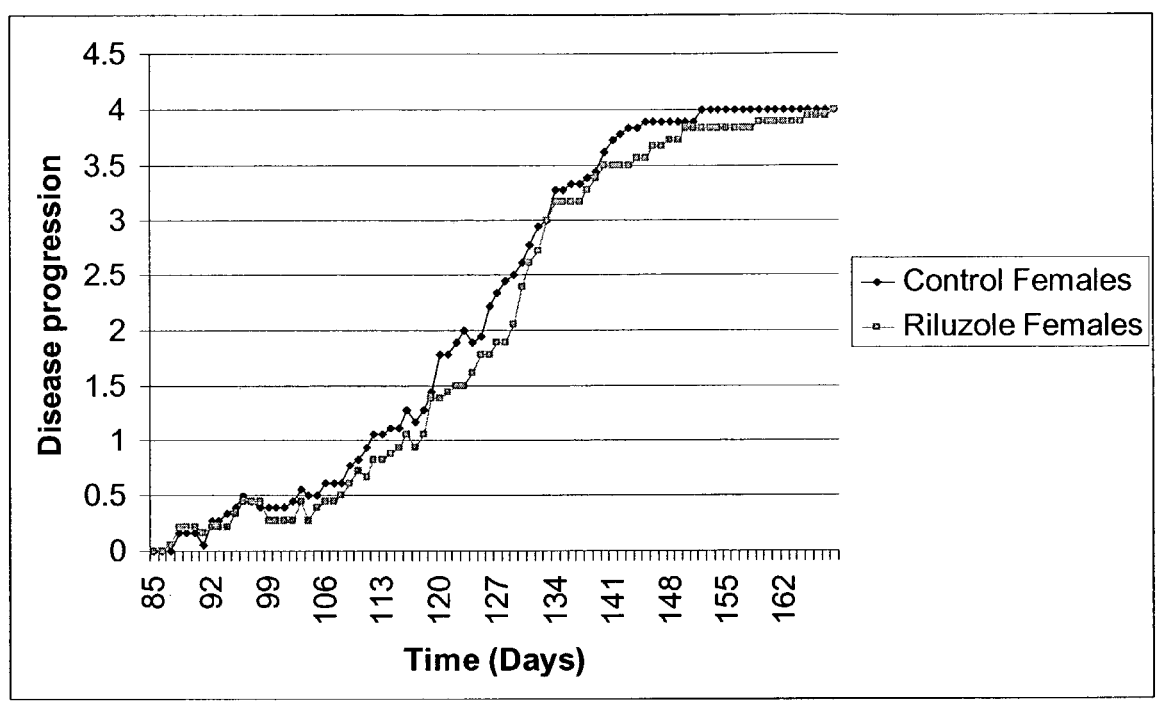
Figure 13: Neuroscore: Combined Females: Riluzole @20 mg/Kg.

Figure 14: Neuroscore: Combined Females: Riluzole @20 mg/Kg.
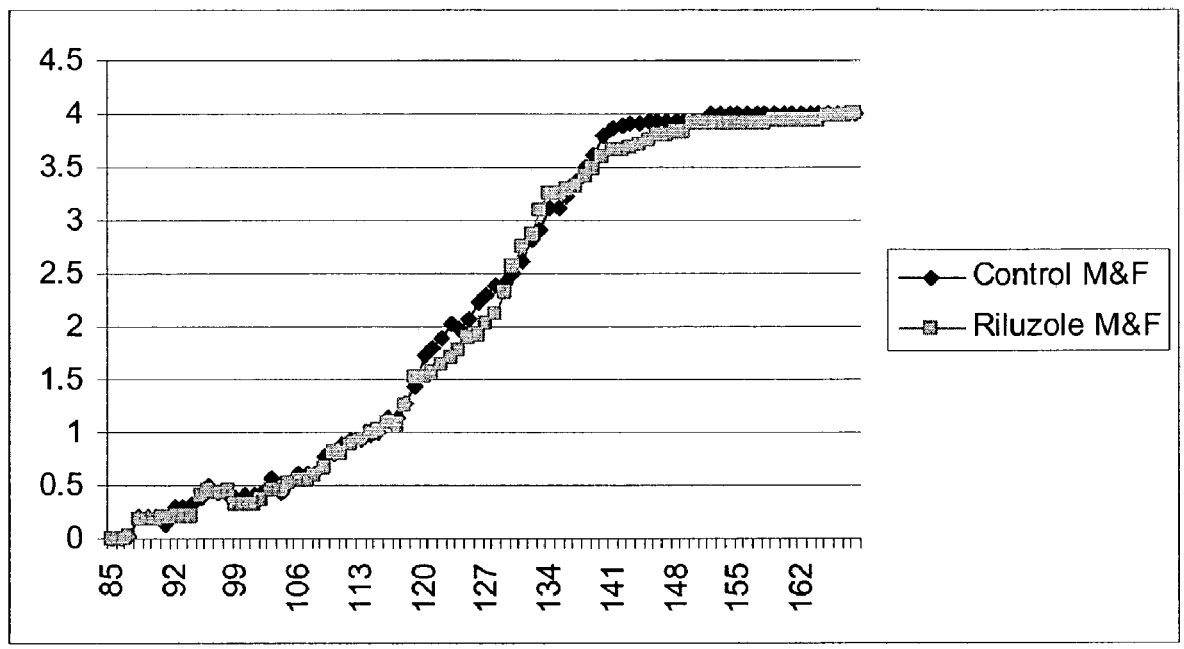

TREATMENT OF NEURODEGENERATIVE DISEASES USING PROTEASOME MODULATORS

REFERENCE TO RELATED APPLICATIONS

This application claims priority to U.S. provisional application No. 60/385,625 filed Jun. 3, 2002, and U.S. provisional application No. 60/385,489, filed: Jun. 3, 2002, which are hereby incorporated by reference.

BACKGROUND OF THE INVENTION

The technical field of the invention concerns methods and compositions for the treatment of neurodegenerative diseases by proteasome modulators.

The proteasome (also known as macropain, the multicatalytic protease, and 20S protease) is a high molecular weight, multisubunit protease which has been identified in every examined species from an archaebacterium to human. The enzyme has a native molecular weight of approximately 650,000 and, as revealed by electron microscopy, a distinctive cylinder-shaped morphology (Rivett, (1989) *Arch. Biochem. Biophys.* 268:1-8; and Orlowski, (1990) *Biochemistry* 29:10289-10297). The proteasome subunits range in molecular weight from 20,000 to 35,000 (3-5), and are homologous to one another but not to any other known protease.

The proteasome enzyme is "multicatalytic," i.e. it has at least three distinctly different catalytic sites including: a peptidylglutamyl-peptide hydrolyzing site, which cleaves peptides with glutamic acid in the P1 position (e.g. CBZ-Leu-Leu-Glu-X); a "trypsin-like" site, which cleaves peptides with basic amino acids in the P1 position (e.g. CBZ-Val-Leu-Arg-X); and a "chymotrypsin-like" site, which cleaves peptides with leucine or other hydrophobic amino acids in the P1 position (e.g. CBZ-Gly-Gly-Leu-X). The proteasome has been identified in both cytoplasmic and nuclear compartments and appears to play a central role in non-lysosomal pathways of intracellular protein degradation, including those mediated by ATP and ubiquitin (McGuire, et al. (1988) *Arch. Biochem. Biophys.* 262:272-285; McGuire, et al. (1989) *Biochim. Biophys. Acta* 967:195-203; McGuire, et al. (1989) *Biochem. Biophys. Res. Commun.* 160:911-916; DeMartino, et al. (1991) *Biochim. Biophys. Acta* 1073:299-308; and Hershko et al. (1992) *Ann. Rev. Biochem.* 61:761-807). Its activity is high in muscle wasting diseases that involve protein breakdown such as muscular dystrophy, cancer and AIDS. Evidence also suggests a possible role for the proteasome in the processing of antigens for the class I MHC molecules (Goldberg, et al. (1992) *Nature* 357:375-379).

Proteasomes may be involved in neurodegenerative diseases and disorders such as Amyotrophic Lateral Sclerosis (ALS). Neurodegenerative diseases are generally characterized by a degeneration of neurons in either the brain or the nervous system of an individual. In addition to ALS, various other diseases, such as Huntington's disease, Parkinson's disease, Alzheimer's disease and Multiple Sclerosis, fall within this category. These diseases are debilitating and the damage that they cause is often irreversible. Moreover, in the case of a number of these diseases, the outcome is invariably fatal.

Progress is being made on many fronts to find agents that can arrest the progress of these diseases. Nonetheless, the present therapies for most, if not all, of these diseases provide very little relief.

Accordingly, a need exists to develop therapies that can alter the course of neurodegenerative diseases or, in the case of diseases like ALS, prolong the survival time of patients with such diseases. More generally, a need exists for better methods and compositions for the treatment of neurodegenerative diseases in order to improve the quality of the lives of those afflicted by such diseases.

SUMMARY OF INVENTION

Methods and compositions for treatment of neurodegenerative diseases by modulating the activity of proteasomes within neural cells are disclosed. Within such cells, the proteasome is the biological machinery that is responsible for normal degradation of proteins. Abnormal proteasome activity in neuronal cells is a contributing factor in neurodegenerative diseases such that the cells lose their ability to adequately degrade proteins, especially the mutated or misfolded proteins that may be pathological components of neurodegenerative diseases. Insofar as loss of function, or change in function, of the proteasome is a contributing factor in neuron degeneration, it has been discovered that certain protease inhibitors, such as Ritonavir® and related compositions, can be useful in restoring desired proteasome activity.

Also disclosed are diagnostic and prognostic screening assays that identify a subject's propensity for a neurodegenerative disorder associated with aberrant proteasome activity, as well as agents that modify the proteasome activity. These assays can also be used to monitor the changes in the neurodegenerative disorder during and after therapy.

Accordingly, in one aspect, the invention pertains to a method for ameliorating the symptoms or progression of a neurodegenerative disease in a subject by administering a therapeutically effective amount of a proteasome modulating pharmacological agent to the subject; and monitoring the amelioration in the symptoms and progression of the neurodegenerative disease. The neurodegenerative disease can be selected from the group consisting of Amyotrophic Lateral Sclerosis (ALS), Parkinson's disease, Huntington's disease and Alzheimer's disease. In one embodiment, the proteasome modulating pharmacological agent is protease inhibitor. The protease inhibitor can be selected from the group consisting of Ritonavir®, lopinavir, nelfinavir, saquinavir, statine, amprenavir, indinavir, lasinavir, palinavir, tipranavir, and azacyclic urea. In a preferred embodiment, the protease inhibitor is Ritonavir®. In one embodiment, the step of monitoring the amelioration of the neurodegenerative disease comprises monitoring survival prolongation of the subject, or group of subjects. In another embodiment, the step of monitoring the amelioration of the neurodegenerative disease comprises monitoring a neurological score/neurological function of the subject, or group of subjects. In yet another embodiment, the step of monitoring the amelioration of the neurodegenerative disease comprises monitoring expression levels of a proteasome subunit associated with the neurodegenerative disease. The proteasome subunit associated with the neurodegenerative disease can be selected from the group consisting of LMP-2, LMP-7 and MECL-1. The expression levels can be monitored by monitoring the protein expression level of the proteasome subunit associated with a neurodegenerative disease. Alternatively, the expression levels can be monitored by monitoring the nucleic acid (e.g., RNA or DNA) expression levels of the proteasome subunit associated with a neurodegenerative disease. In yet another embodiment, the amelioration of the symptoms, or progression of the neurodegenerative disease comprises modifying a target in a cell, wherein the target is involved in a pathway associated with the neurodegenerative disease. For example, the target can be a proteasome (e.g., 20S proteasome) or a proteasome subunit associated with the neurodegenerative disease (e.g., LMP-2, LMP-7, or MECL-1).

In another aspect, the invention pertains to a method for modulating proteasome activity in a subject associated with a neurodegenerative disease by administering a therapeutically effective amount of a proteasome modulating pharmacological agent to the cell; and monitoring the modulation of proteasome activity in the subject. In one embodiment, the neurodegenerative disease is selected from the group consisting of Amyotrophic Lateral Sclerosis (ALS), Huntington's disease and Parkinson's disease. In a preferred embodiment, the neurodegenerative disease is ALS. In one embodiment, the proteasome modulating pharmacological agent is a protease inhibitor selected from the group consisting of Ritonavir®, lopinavir, nelfinavir, saquinavir, statine, amprenavir, indinavir, lasinavir, palinavir, tipranavir, and azacyclic urea. In a preferred embodiment, the proteasome modulating pharmacological agent is protease inhibitor, such as Ritonavir®. In one embodiment, the step of monitoring the modulation of proteasome activity comprises monitoring survival prolongation of the subject, or group of subjects. In another embodiment, the step of monitoring the modulation of proteasome activity comprises monitoring a neurological score/neurological function of the subject, or group of subjects. In yet another embodiment, the step of monitoring the modulation of proteasome activity comprises monitoring expression levels of a proteasome subunit associated with a neurodegenerative disorder, such as LMP-2, LMP-7 and MECL-1. The expression levels can be monitored by monitoring the protein level of the proteasome subunit associated with a neurodegenerative disorder. Alternatively, the expression levels can be monitored by monitoring the nucleic acid levels (e.g., RNA or DNA) of the proteasome subunit associated with a neurodegenerative disorder.

In yet another aspect, the invention pertains to a method for detecting a pharmacological agent that modulates proteasome activity in a cell associated with a neurodegenerative disease, by determining a level of proteasome activity in a sample, applying a pharmacological agent to the sample, and measuring a change in the level of proteasome activity in response to the applied pharmacological agent. The step of determining proteasome activity may further comprise determining the expression level of a proteasome subunit associated with a neurodegenerative disease, such as LMP-2, LMP-7 and MECL-1. The pharmacological agent can be a known proteasome inhibitor, a protease inhibitor, or an unknown proteasome modulator. A change in the level of proteasome activity in response to the applied pharmacological agent comprises measuring a change in the expression level of a proteasome subunit associated with a neurodegenerative disease. For example, if the proteasome subunit associated with a neurodegenerative disease is LMP-2, LMP-7 and MECL-1, a decrease in the expression level of the proteasome subunit indicates that the pharmacological agent modulates proteasome activity.

In yet another aspect, the invention pertains to a method of assessing whether a subject is afflicted with a neurodegenerative disorder, the method by comparing the level of proteasome activity in a test sample from a subject, and the normal level of proteasome activity in a control sample, wherein a significant difference between the level of proteasome activity in the sample from the subject and the normal level is an indication that the subject is afflicted with a neurodegenerative disorder. The test sample is obtained from a subject suspected of having a neurodegenerative disorder selected from the group consisting of ALS, Parkinson's disease, and Huntington's disease.[ ]

In yet another aspect, the invention pertains to a method for monitoring the progression of a neurodegenerative disorder in a subject, by (a) detecting a level of proteasome activity in a subject sample at a first time point; (b) repeating step (a) at a subsequent point in time; and (c) comparing the expression levels of proteasome activity detected in steps a) and b), and therefrom monitoring the progression of the neurodegenerative disorder in the subject.

BRIEF DESCRIPTION OF FIGURES

FIG. 1 is a photograph of a Northern blot showing expression of the LMP-7 proteasomal subunit in N2A neuroblastoma cells lines expressing the SOD1 mutation.

FIG. 2 is a photograph of a Northern blot showing expression of the MECL-1 proteasomal subunit in N2A neuroblastoma cells lines expressing the SOD1 mutation.

FIG. 3 is a graph showing the effects of Ritonavir on the survival of male and female SOD1 G93A mouse models of ALS;

FIG. 4 is a graph showing the effects of Ritonavir on the survival of male SOD1 G93A mouse models of ALS;

FIG. 5 is a graph showing the effects of Ritonavir on the survival of female SOD1 G93A mouse models of ALS;

FIG. 6 is a graph showing the effects of Riluzole on the survival of male and female SOD1 G93A mouse models of ALS;

FIG. 7 is a graph showing the effects of Riluzole on the survival of male SOD1 G93A mouse models of ALS;

FIG. 8 is a graph showing the effects of Riluzole on the survival of female SOD1 G93A mouse models of ALS;

FIG. 9 is a graph showing the neurological score of combined male SOD1 G93A mouse models of ALS treated with Ritonavir;

FIG. 10 is a graph showing the neurological score of combined female SOD1 G93A mouse models of ALS treated with Ritonavir;

FIG. 11 is a graph showing the neurological score of combined male and female SOD1 G93A mouse models of ALS treated with Ritonavir; and FIG. 12 is a graph showing the neurological score of combined male SOD1 G93A mouse models of ALS treated with Riluzole;

FIG. 13 is a graph showing the neurological score of combined female SOD1 G93A mouse models of ALS treated with Riluzole; and FIG. 14 is a graph showing the neurological score of combined male and female SOD1 G93A mouse models of ALS treated with Riluzole.

DETAILED DESCRIPTION

So that the invention is more clearly understood, the following terms are defined:

The term "neurodegenerative disorder" or "neurodegenerative disease" are used interchangeably herein and refer to an impairment or absence of a normal neurological function, or presence of an abnormal neurological function in a subject, or group of subjects. For example, neurological disorders can be the result of disease, injury, and/or aging. As used herein, neurodegenerative disorder also includes neurodegeneration which causes morphological and/or functional abnormality of a neural cell or a population of neural cells. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, Amyotrophic Lateral Sclerosis (ALS), multiple sclerosis, Huntington's disease, Parkinson's disease, Alzheimer's disease, prion associated disease (CJD), spinal muscular atrophy, spinal cerebellar ataxia, and spinal cord injury.

The terms "modulate" or "modulating" or "modulated" are used interchangeable herein and refer to a change in the proteasome activity, structure, or the expression of a proteasome, or a subunit of the proteasome, i.e., an increase or decrease in proteasome activity, or expression, such that the modulation produces a therapeutic effect in a subject, or group of subjects. A therapeutic effect is one that results in an amelioration in the symptoms, or progression of the neurodegenerative disease. These terms also refers to modifying the proteolytic function of the proteasome. The change in activity can be reflected in terms of the expression of at least one subunit of the proteasome, and the change in expression can be measured by quantitative or qualitative measurements of the protein level of the proteasome or a proteasome subunit, for example by Western blot analysis. The quantitative assay can be used to measure downregulation or upregulation of a proteasome subunit in the presence of a protease inhibitor, such as Ritonavir® A suitable protease inhibitor can be one that down-regulates proteasome subunit expression by about 5 percent to about 50 percent compared with a control. A suitable proteasome activator that up-regulates a proteasome subunit, is one that up-regulates proteasome subunit expression by about 5 percent to about 50 percent compared with a control.

The change in expression can also be measured by quantitative or qualitative measurements of the nucleic acid level associated with the proteasome or a proteasome subunit, for example by measuring the expression level of RNA or DNA. The change in the proteolytic activity of the proteasome can be determined by examining the proteolysis of peptides or proteins by the proteasome. For example, by examining the hydrolysis of fluorogenic substrates by the proteasomes in the presence of a protease inhibitor (e.g., Ritonavir, which inhibits the chymotrypsin-like activity of the proteasome), or by examining antigen presentation of the proteasome, or a subunit of the proteasome (See e.g., Andre et al. (1998) *Proc Natl Acad Sci* USA 95:13120-4).

The effect of proteasome modulation on a subject, or group of subjects, can also be investigated by examining the survival of the subject, or group of subjects. For example, by measuring the change in the survival, or the prolongation of survival in one or more animal models for a neurodegenerative disease. The change in the survival can be due to the administration of a proteasome modulator such as a protease inhibitor that is administered to an ALS murine model. The effect of the protease inhibitor on the proteasome can be determined based on the increase in days of survival of a test group of ALS mice compared with a control group of ALS mice that have been given a control agent (e.g., Riluzole), or no agent. In one embodiment, the proteasome modulating agent increases the percentage effect on survival of the subject, or a population of subjects (e.g., a male population, or a female population) by at least 2% to about 100%. Preferably the percentage effect on survival of the subject, or a population of subjects, is by at least 5% to about 50%, by at least 10% to about 25%. Even more preferably, the percentage effect on survival of the subject, or a population of subjects, is by at least 3%, 4%, 5%, 6%, 7%, 8%, 9%, 10%, 12%, 14%, 16%, 18%, 20%, 22%, 24%, 26% 28%, 30%, 32%, 34%, 36%, 38%, 40%, 42%, 44%, 46%, 48% and 50%. The effect of proteasome modulation may also determined by examining the neurological score of a subject, or group of subjects for example, by assessing the improvement in muscular movement, or by examining the alleviation or amelioration of the disease symptoms. In a preferred embodiment, the neurological score of a subject, or group of subjects is significantly different from that of the untreated control subjects, with a level of significance between $p<0.05$ and $p<0.0001$, as determined using standard statistical analysis procedures.

The terms "pharmacological agent" and "proteasome modulating pharmacological agent" as used herein, are intended to be used interchangeably, and these terms refer to the compound, or compounds, that are used to modulate the proteasome activity in a subject. Preferably, the proteasome modulating pharmacological agent is a protease inhibitor, for example, the protease inhibitors approved by the Food and Drug Administration, as well as the protease inhibitors disclosed in Piccinini, et al., (2002) *AIDS*, 16: 693-700), the contents of which are herein incorporated in their entirety by reference. In a preferred embodiment, the proteasome modulating pharmacological agent is the compound Ritonavir®, also known as Norvir®, which is chemically designated as 10-Hydroxy-2-methyl-5-(1-methylethyl)-4-thiazolyl]-3,6-dioxo-8,11-bis (phenylmethyl)-2,4,7,12-tetraazatridecan-13-oic acid, 5-thiazolylmethyl ester, [5S-(5R*,8R*,10R*, 11R*)]. Other pharmacological agents include analogs and variants of the compound Ritonavir®, as disclosed in U.S. Pat. Nos. 5,491,253 and 5,541,206, as well as in Kempf et al., (1995) *Proc. Natl. Acad. Sci. U.S.A.*, 92: 2484-2488, the contents of which are herein expressly incorporated in their entirety by reference. The terms "pharmacological agent" or "proteasome modulating pharmacological agent" are also intended to include other HIV protease inhibitors with a similar structure and function to Ritonavir®.

The terms "ritonavir" or "Ritonavir®" refers to the compound that is chemically designated as 10-Hydroxy-2-methyl-5-(1-methylethyl)-4-thiazolyl]-3,6-dioxo-8,11-bis (phenylmethyl)-2,4,7,12-tetraazatridecan-13-oic acid, 5-thiazolylmethyl ester, [5S-(5R*,8R*,10R*,11R*)], has a molecular formula of $C_{37}H_{48}N_6O_5S_2$, has a molecular weight of 720.95, and has the following chemical structure:

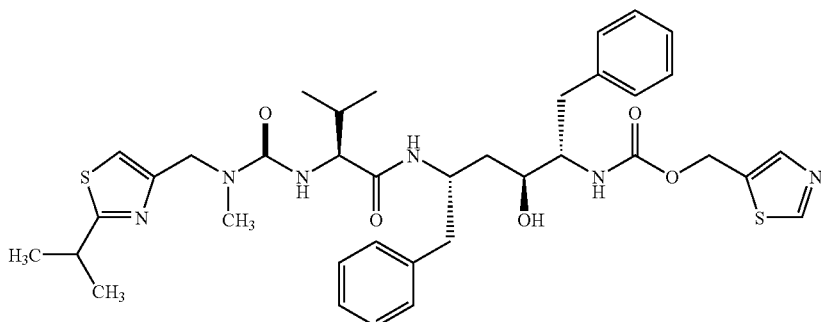

The terms "ritonavir" or "Ritonavir®" are also intended to cover all synonyms for the compound listed above. Such synonyms include, for example, Norvir®; 5-Thiazolylmethyl ((alphas-alpha-((1S,3S-1-hydroxy-3-((2S-2-(3-((2-isopropyl-4-thiazolyl)methyl)-3-methylureido)-3-methylbutyramido)-4-phenylbutyl)phenethyl)carbamate; A-84538; ABT-538; Abbott 84538; DRG-0244; 2,4,7,12-Tetraazatridecan-13-oic acid, 10-hydroxy-2-methyl-5-(1-methylethyl)-1-(2(1-methylethyl)-4-thiazolyl)-3,6-dioxo-8,11-bis (phenylmethyl)-5-thiazolylymethyl ester, (5S-(5R*,8R*,10R*,11R*)); compounds having the molecular formula $C_{37}H_{48}N_6O_5S_2$; and Thiazol-5-ylmethyl (1S,2S,4S)-1-benzyl-2-hydroxy-4-((2S)-2-[2-isopropylthiazol-4-ylmethyl)-3-methylureido]-3-methylbutyramido)-5-phenylpentylcarbamate. A suitable dosage of Ritonavir® in an ALS mouse model is about 10-60 mg/kg/day, similar to a dosage of about 100-1200 mg/day in a human subject.

The term "sample" as used herein refers to a normal cell line, while in an alternative embodiment, the term "sample" refers to a mutant cell line having altered levels of proteasome activity. By way of non-limiting example, the mutant cell line can be a cell line that carries the human G9A SOD mutation and is driven by the endogenous promoter. In yet another embodiment, the term "substrate" refers to an isolated proteasomes. These proteasome can be isolated from a variety of tissues and use as a substrate.

As used herein, the term a "test sample" or a "biological test sample" includes a biological sample obtained from a subject of interest. For example, a test sample can be a biological fluid (e.g., blood), cell sample, or tissue (e.g., skin).

The term "level of proteasome activity" or "proteasome activity," which are intended to be used interchangeably herein, refers to the expression of a variety of markers that indicate the level of proteasome function within a subject or substrate. By way of non-limiting example, suitable markers for indicating the level of proteasome activity in a subject or substrate include expression of the proteasome subunits, such as LMP-2, LMP-7 and MECL-1, the expression of MHC Class I antigens on the cell surface, as well as various cell cycle proteins, such as for example, CDK5, Jak3 kinase and NfkappaB.

The term "measuring changes in the level of proteasome activity" or "measuring changes in proteasome activity," as used herein, refers to any means or methods of comparison between the level of proteasome activity in a substrate prior to the application of a pharmacological agent and the level of proteasome application after application of the pharmacological agent.

The term "therapeutically effective amount" refers to an amount effective, at dosages and for periods of time necessary, to achieve the desired therapeutic result. A therapeutically effective amount of the proteasome modulating pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

For example, the dosage of a protease inhibitor such as Ritonavir®, to be administered may be determined by one skilled in the art, and will vary with the type of treatment modality and extent of disease. A useful therapeutic dosage range for Ritonavir® is about 50 mg/day to about 2000 mg/day, preferably about 100 mg/day to about 1500 mg/day, more preferably about 100 mg/day to about 1200 mg/day, and most preferably about 300 mg/day to about 400 mg/day. The aim of the administration is to result in a final body dose that ameliorates the symptoms or progression of the neurodegenerative disorder. The amount of Ritonavir® required as daily dose in treatment will vary with the route of administration, the nature of the condition being treated and the age, weight and condition of the patient, and will ultimately be at the discretion of the attendant physician.

The term "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The term "subject" as used herein refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The invention is described in more detail in the following subsections:

I. Neurodegenerative Diseases

Evidence is accumulating that as a result of the normal aging process the body increasingly loses the ability to adequately degrade mutated or misfolded proteins. The proteasome is the piece of biological machinery that is responsible for most normal degradation of proteins found inside cells. Age-related loss of function, or change in function of the proteasome is now thought to be at the heart of many neurodegenerative conditions, including, for example, amyotrophic lateral sclerosis (ALS), Alzheimer's disease, Parkinson's disease, Huntington's disease, and Multiple Sclerosis, each of which is described below.

(a) Amyotrophic Lateral Sclerosis

Amyotrophic Lateral Sclerosis (ALS), also called Lou Gehrig's disease, is a fatal neurodegenerative disease affecting motor neurons of the cortex, brain stem and spinal cord. (Hirano, (1996) *Neurology*, 47(4 Suppl. 2): S63-6). Onset of ALS occurs in the fourth or fifth decade of life (median age of onset is 57) and is fatal within two to five years after diagnosis (Williams, et al. (1991) *Mayo Clin. Proc.*, 66: 54-82). ALS affects approximately 30,000 Americans with nearly 8,000 deaths reported in the US each year. ALS patients progressively lose all motor function—unable to walk, speak, or breathe on their own.

The cardinal feature of ALS is the loss of spinal motor neurons, which causes the muscles under their control to weaken and waste away leading to paralysis. ALS has both familial (5-10%) and sporadic forms and the familial forms have now been linked to several distinct genetic loci (Deng, et al. (1995) *Hum. Mol. Genet.*, 4: 1113-16; Siddique, et al. (1995) *Clin. Neurosci.*, 3: 338-47; Siddique, et al., (1997) *J. Neural Transm. Suppl.*, 49: 219-33; Ben Hamida, et al. (1990) *Brain*, 113: 347-63; Yang, et al. (2001) *Nat. Genet.* 29: 160-65; Hadano, et al. (2001) *Nat. Genet.* 29: 166-73). About 15-20% of familial cases are due to mutations in the gene encoding Cu/Zn superoxide dismutase 1 (SOD1) (Siddique, et al. (1991) *N. Engl. J. Med.*, 324: 1381-84; Rosen, et al. (1993) *Nature*, 362: 59-62).

Although the etiology of the disease is unknown, one theory is that neuronal cell death in ALS is the result of over-excitement of neuronal cells due to excess extracellular glutamate. Glutamate is a neurotransmitter that is released by glutaminergic neurons, and is taken up into glial cells where it is converted into glutamine by the enzyme glutamine synthetase, glutamine then re-enters the neurons and is hydrolyzed by glutaminase to form glutamate, thus replenishing the neurotransmitter pool. In a normal spinal cord and brain stem, the level of extracellular glutamate is kept at low micromolar levels in the extracellular fluid because glial cells, which function in part to support neurons, use the excitatory amino acid transporter type 2 (EAAT2) protein to absorb glutamate immediately. A deficiency in the normal EAAT2 protein in patients with ALS, was identified as being important in the pathology of the disease (See e.g., Meyer et al. (1998) *J. Neurol. Neurosurg. Psychiatry*, 65: 594-596; Aoki et al. (1998) *Ann. Neurol.* 43: 645-653; Bristol et al. (1996) *Ann Neurol.* 39: 676-679). One explanation for the reduced levels of EAAT2 is that EAAT2 is spliced aberrantly (Lin et al. (1998) *Neuron*, 20: 589-602). The aberrant splicing produces a splice variant with a deletion of 45 to 107 amino acids located in the C-terminal region of the EAAT2 protein (Meyer et al. (1998) *Neureosci Lett.* 241: 68-70). Due to the lack of, or defectiveness of EAAT2, extracellular glutamate accumulates, causing neurons to fire continuously. The accumulation of glutamate has a toxic effect on neuronal cells because continual firing of the neurons leads to early cell death.

Although a great deal is known about the pathology of ALS little is known about the pathogenesis of the sporadic form and about the causative properties of mutant SOD protein in familial ALS (Bruijn, et al. (1996) *Neuropathol. Appl. Neurobiol.*, 22: 373-87; Bruijn, et al. (1998) *Science* 281: 1851-54). Many models have been speculated, including glutamate toxicity, hypoxia, oxidative stress, protein aggregates, neurofilament and mitochondrial dysfunction Cleveland, et al. (1995) *Nature* 378: 342-43; Cleveland, et al. *Neurology*, 47(4 Suppl. 2): S54-61, discussion S61-2(1996); Cleveland, (1999) *Neuron,* 24: 515-20; Cleveland, et al. (2001) *Nat. Rev. Neurosci.*, 2: 806-19; Couillard-Despres, et al. (1998) *Proc. Natl. Acad. Sci. USA*, 95: 9626-30; Mitsumoto, (1997) *Ann. Pharmacother.*, 31: 779-81; Skene, et al. (2001) *Nat. Genet.* 28: 107-8; Williamson, et al. (2000) *Science*, 288: 399).

Presently, there is no cure for ALS, nor is there a therapy that has been proven effective to prevent or reverse the course of the disease. Several drugs have recently been approved by the Food and Drug Administration (FDA). To date, attempts to treat ALS have involved treating neuronal degeneration with long-chain fatty alcohols which have cytoprotective effects (See U.S. Pat. No. 5,135,956); or with a salt of pyruvic acid (See U.S. Pat. No. 5,395,822); and using a glutamine synthetase to block the glutamate cascade (See U.S. Pat. No. 5,906,976). For example, Riluzole™, a glutamate release inhibitor, has been approved in the U.S. for the treatment of ALS, and appears to extend the life of at least some patients with ALS. However, some reports have indicated that even though Riluzole™ therapy can prolong survival time, it does not appear to provide an improvement of muscular strength in the patients. Therefore, the effect of Riluzole™ is limited in that the therapy does not modify the quality of life for the patient (Borras-Blasco et al. (1998) Rev.*Neurol.*, 27: 1021-1027).

Evidence is accumulating that as a result of the normal aging process the body increasingly loses the ability to adequately degrade mutated or misfolded proteins. The proteasome is the piece of biological machinery responsible for most normal degradation of proteins inside cells. Age related loss of function or change of function of the proteasome appears to be involved in neurodegenerative conditions, as shown in the Examples section.

(b) Multiple Sclerosis

Multiple Sclerosis (MS) is a chronic disease that is characterized by "attacks," during which areas of white matter of the central nervous system, known as plaques, become inflamed. Inflammation of these areas of plaque is followed by destruction of myelin, the fatty substance that forms a sheath or covering that insulates nerve cell fibers in the brain and spinal cord. Myelin facilitates the smooth, high-speed transmission of electrochemical messages between the brain, spinal cord, and the rest of the body. Damage to the myelin sheath can slow or completely block the transmission of these electrochemical messages, which can result in diminished or lost bodily function.

The most common course of MS manifests itself as a series of attacks, which are followed by either complete or partial remission, during which the symptoms lessen only to return at some later point in time. This type of MS is commonly referred to as "relapsing-remitting MS." Another form of MS, called "primary-progressive MS," is characterized by a gradual decline into the disease state, with no distinct remissions and only temporary plateaus or minor relief from the symptoms. A third form of MS, known as "secondary-progressive MS," starts as a relapsing-remitting course, but later deteriorates into a primary-progressive course of MS.

The symptoms of MS can be mild or severe, acute or of a long duration, and may appear in various combinations. These symptoms can include vision problems such as blurred or double vision, red-green color distortion, or even blindness in one eye, muscle weakness in the extremities, coordination and balance problems, muscle spasticity, muscle fatigue, paresthesias, fleeting abnormal sensory feelings such as numbness, prickling, or "pins and needles" sensations, and in the worst cases, partial or complete paralysis. About half of the people suffering from MS also experience cognitive impairments, such as for example, poor concentration, attention, memory and/or judgment. These cognitive symptoms occur when lesions develop in those areas of the brain that are responsible for information processing.

Experimental autoimmune encephalomyelitis (EAE) is an experimental autoimmune disease of animals that is thought to model aspects of multiple sclerosis (Zamvil et al. (1990) *Annu. Rev. Immunol*. 8: 579-621). EAE can be induced in susceptible strains of rats, such as the Lewis rat, by immunization to myelin basic protein (MBP) in complete Freund's adjuvant (CFA), an emulsion of mineral oil containing killed Mycobacteria. The disease develops about 12 days after immunization and is characterized by paralysis of various degrees due to inflammation of the central nervous system. The paralysis can last up to 6 or 7 days and the rats usually recover unless they die during the peak of their acute paralysis. EAE is caused by T cells that recognize defined determinants of the MBP molecule. The major MBP determinant in the Lewis rat is composed of the peptide sequence 71-90 (Zamvil et al. Supra).

Alternatively, in vitro cell lines for MS can also be used. Such in vitro cell lines include, but are not limited to, the LM7PC and PLI-2 cell lines. These two continuous cell lines were derived from human choroid plexus cells originating from two different patients suffering from MS obtained by a culture method described in the document WO-A-9320188 and U.S. Pat. No. 6,342,383 to Perron et al.

(c) Alzheimer's Disease

Alzheimer's disease is a progressive, neurodegenerative disease that affects the portions of the brain that control thought, memory and language. This disease is characterized by progressive dementia that eventually results in substantial impairment of both cognition and behavior. The disease manifests itself by the presence of abnormal extracellular protein deposits in brain tissue, known as "amyloid plaques," and tangled bundles of fibers accumulated within the neurons, known as "neurofibrillary tangles," and by the loss of neuronal cells. The areas of the brain affected by Alzheimer's disease can vary, but the areas most commonly affected include the association cortical and limbic regions. Symptoms of Alzheimer's disease include memory loss, deterioration of language skills, impaired visuospatial skills, and impaired judgment, yet those suffering from Alzheimer's retain motor function.

Alzheimer's disease is characterized by two hallmark pathological features that involve protein misfolding: Neurofibrillary tangles (NFTs) formed by paired helical filaments (PHFs) from abnormally modified Tau protein and senile plaques composed of beta-amyloid (Aβ) (See Price, et al., (1998) *Annu Rev Neurosci* 21: 479-505). Mild cognitive impairment (MCI) is observed in Alzheimer's disease and is thought to represent the prodromal stage of Alzheimer's disease. MCI accompanies neuronal loss in Alzheimer's disease. Dementia and neuronal loss in Alzheimer's disease correlate significantly with levels of Tau pathology and resulting NFTs. Evidence for altered/reduced proteasomal activity in Alzheimer's disease has been found that may result from the defective ubiquination and/or breakdown of misfolded proteins such as PHF-Tau and beta amyloid by the 20S proteasome (Keck, et al. (2003) *J Neurochem* 85:115-22; Keller et al. (2000) *J Neurochem* 75: 436-9; and Lopez et al., (2003) *Exp Neurol* 180: 131-43). Additionally, a mutant form of ubiquitin (Ub+1), generated by molecular misreading, was observed in the brains of Alzheimer's disease patients including those with the non-familial Alzheimer's disease (van Leeuwen, et al. (1998) *Science* 279: 242-7; and Lam, et al., (2000) *Proc Natl Acad Sci U S A* 97: 9902-6). Ub+1 capped polyUb chain was also able to inhibit proteasomal activity in vitro and may induce accumulation of misfolded proteins and contribute to both Aβ and Tau pathology in Alzheimer's disease (Lam, et al., (2000) Supra).

Proteasomal dysregulation can lead to a variety of cellular alterations that can contribute to chronic neurodegeneration some of which include polyamine dysregulation and cell cycle dysregulation, inflammation and apoptosis (See e.g., Jesenberger, et al. (2002) *Nat Rev Mol Cell Biol* 3: 112-21; Li, et al. (2003) *Int J Biochem Cell Biol* 35: 547-52; Bernstein, et al. (1995) *Neurosci Lett* 186:123-6; and Trojanowski et al. (2000) *Ann N Y Acad Sci* 924: 62-7). Expression of cell cycle regulating gene products and induction of DNA replication (clear indications of cell cycle re-entry) has been demonstrated in Alzheimer's disease and Parkinson's disease (Jordan-Sciutto, et al. (2002) *J Neuropathol Exp Neurol* 61: 358-67; Klein, et al. (2003) *J Clin Invest* 111: 785-93; Nouspikel, et al. (2003) *Bioessays* 25: 168-73; and Yang, et al. (2001) *J Neurosci* 21: 2661-8). Most recently Yang et al demonstrated that the cell cycle induction in Alzheimer's disease is observed during both the early prodromal stage (MCI) and in the advanced stages of Alzheimer's disease indicating that neurons dwell in an unproductive cell cycle for many months before finally committing to apoptosis (Yang, et al. (2003) *J Neurosci* 23: 2557-63). The protective effect of flavopiridol, a pan-CDK inhibitor, in a model of proteasome inhibition-induced neuronal death, together with the finding of cycling CDK induction in an in vitro Aβ model of Alzheimer's disease demonstrate a link between proteasomal dysfunction and cell cycle dysregulation and neuronal death (Jordan-Sciutto, et al. (2001) *Mech Ageing Dev* 123: 11-20; and Rideout, et al. (2003) *J Neurosci* 23: 1237-45).

A suitable animal model for Alzheimer's disease that mimics the pathology of the disease in humans can be one in which a selective lesion is placed in a subcortical nucleus (nucleus basalis of Meynert) with a resultant cortical cholinergic deficiency, similar in magnitude to that seen in early to moderate stage Alzheimer's disease. Numerous behavioral deficits, including the inability to learn and retain new information, are characteristic of this lesion. Pharmacological agents that can normalize these abnormalities would have a reasonable expectation of efficacy in Alzheimer's disease (See e.g., Haroutunian, et al. (1985) *Life Sciences*, 37:945-952).

In addition to in vivo models, a number of in vitro cell lines can also be used to examine the effects of pharmacological agents on Alzheimer's disease such as apolipoprotein E uptake and low-density lipoprotein receptor-related protein expression by the NTera2/D1 cell line, a cell culture model for late-onset Alzheimer's disease (See e.g., Williams et al. (1997) *Neurobiol. of Disease*, 4:58-67). Alternatively, human melanocytes can be used as a model system for studies of Alzheimer's disease (See e.g., Yaar et al. (1997) *Arch. Dermatol*. 133:1287-291).

(d) Parkinson's Disease

Parkinson's disease is a motor system disorder caused by the loss of nerve cells, or neurons, found in the substantia nigra region of the mid-brain. These neurons produce dopamine, a chemical messenger molecule that is found in the brain and helps control or direct muscle activity. Dopamine is used by the cells of the substantia nigra as a neurotransmitter to signal other nerve cells. Parkinson's disease occurs when these neurons die or become impaired, thereby decreasing dopamine levels within the brain. Loss of dopamine causes the neurons to fire uncontrollably, which leaves patients unable to direct or control their bodily movement in a normal manner. The four main symptoms of Parkinson's disease are trembling in the hands, arms, legs, jaw and face; stiffness of the limbs and/or trunk; a slowness of movement, referred to as bradykinesia; and impaired balance and/or coordination. Parkinson's disease is both chronic, i.e., it persists over a long period of time, and progressive, i.e., the symptoms grow worse over time.

Animal models of Parkinson's disease are well established, such as the primate model of Parkinson's Disease described by Zamir et al. (1984) *Brain Res*. 322, 356-60. Neurodegenerative disease-causing substance can be used to cause a neurodegenerative disease in a mammal. Examples of such substances include N-methyl-4-phenyl-1,2,3,6-tetrahydropyridine (MPTP), 1-methyl-4-henylpyridine (MPP$^+$) and manganese dust for Parkinson's disease; quinolinic acid for Huntington's chorea; and beta-N-methylamino-L-alanine for amyotrophic lateral sclerosis, Parkinson's disease and Alzheimer's disease. Due to their mimicry of effects of Parkinson's disease, treatment of animals with methamphetamine or MPTP has been used to generate models for Parkinson's disease. The end result of MPTP administration is the destruction of the striatum in the brain, an area in the neocortex limbic system in the subcortical area in the center of the brain, an area compromised in Parkinson's disease. The neurotransmitter dopamine is concentrated in the striatum Parkinson's disease is characterized by lesions in that area of the brain and by depleted dopamine levels. In some species (primates) the striatal degeneration has been reported to be accompanied by behavioral symptoms that mimic Parkinson's symptoms in humans (See e.g., Markey, et al. (1986) *Medicinal Research Reviews* 6:389-429).

(e) Huntington's Disease

Huntington's disease is a hereditary disorder caused by the degeneration of neurons in certain areas of the brain. This degeneration is genetically programmed to occur in certain areas of the brain, including the cells of the basal ganglia, the structures that are responsible for coordinating movement. Within the basal ganglia, Huntington's disease specifically targets nerve cells in the striatum, as well as cells of the cortex, or outer surface of the brain, which control thought, perception and memory. Neuron degeneration due to Huntington's disease can result in uncontrolled movements, loss of intellectual capacity and faculties, and emotional disturbance, such as, for example, mood swings or uncharacteristic irritability or depression.

As discussed above, neuron degeneration due to Huntington's disease is genetically programmed to occur in certain areas of the brain. Studies have shown that Huntington's disease is caused by a genetic defect on chromosome 4, and in particular, people with Huntington's disease have an abnormal repetition of the genetic sequence CAG in the Huntington's disease gene, which has been termed IT15. The IT15 gene is located on the short arm of chromosome 4 and encodes a protein called huntingtin. Exon I of the IT15 gene contains a polymorphic stretch of consecutive glutamine residues, known as the polyglutamine tract (Rubinsztein, (2002) TRENDS in *Genetics*, 18: 202-9). Asymptomatic individuals typically contain fewer than 35 CAG repeats in the polyglutamine tract. Murine models for HD include that described by Hayden et al. in U.S. Pat. No. 5,849,995, as well as in vitro systems as described in U.S. Pat. No. 5,834,183 to Orr et al.

(f) Prion-Associated Diseases

The prion protein (PrP) is closely associated with a group of fatal neurodegenerative diseases (Ma, et al. (2001) *Proc. Natl. Acad Sci*., 98:14955-14960). This group of disorders is characterized by vacuolation of the brain's gray matter, also known as spongioform change. These diseases can take a variety of forms. For example, these diseases can be sporadic, dominantly heritable, as well as transmissible disorders. In humans, the most prevalent form of prion disease is Creutzfeldt-Jakob disease, while in animals, the most common form is known as scrapie. Other disorders in this group include kuru, Gerstmann-Straussler-Scheinker disease and fetal familial insomnia. All disorders are invariably fatal.

In particular, the symptoms of Creutzfeldt-Jakob disease include a rapidly progressive deterioration of intellectual abilities (also known as dementia). The median duration of this illness, from on-set of symptoms to death is around four months. As the disease state progresses, the dementia is typically accompanied by other symptoms such as ataxia, muscular rigidity, and spontaneous and irregular limb jerks, also known as myoclonus.

(g) Spinocerebellar Ataxia

Ataxias are diseases wherein a person loses the ability to coordinate muscle activity during voluntary muscle contraction, and therefore, loses the ability to coordinate smooth bodily movements. Spinocerebellar ataxia is the most common form of hereditary ataxia. Symptoms of the on-set of spinocerebellar ataxia include limb ataxia, nystagmus (rhythmical oscillation of the eyeballs, in either a pendular or jerky motion), kyphoscoliosis (a deformity of the spine characterized by extensive flexion), and pes cavus (a contracted foot, or exaggeration of the normal arch of the foot). The major pathological changes that occur with the disease state occur in the posterior columns of the spinal cord. Spinocerebellar ataxia is most often an autosomal recessive inherited disorder.

Among the adult-onset dominant spinocerebellar ataxias (SCAs), seven different loci have been mapped (Gispert et al. (1993) *Nature Genet*. 4, 295-299; Takiyama et al. (1993) *Nature Genet*. 4, 300-304; Gardner et al. (1994) *Neurology*, 44: A361; Nagafuchi et al. (1994) *Nature Genet*. 6: 14-18; Ranum et al. (1994) *Nature Genet*. 8, 280-284; Benomar et al. (1995) *Nature Genet*. 10: 84-88; Gouw et al. (1995) *Nature Genet*. 10: 89-93; Zhuchenko et al. (1997) *Nature Genet*. 15: 62-69). Approximately sixty percent of the dominant ataxias result from expansions in trinucleotide CAG repeats at the SCA1, 2, 3, 6 or 7 loci (Nagafuchi et al. (1994) *Nature Genet*. 6: 14-18; Zhuchenko et al. (1997) *Nature Genet*. 15: 62-69; Orr et al. (1993) *Nature Genet*. 4: 211-226; Kawaguchi et al. (1994) *Nature Genet*. 8: 221-228; Koide et al. (1994) *Nature Genet*. 6: 9-13; Imbert et al. (1996) *Nature Genet*. 14: 285-291; Pulst et al. (1996) *Nature Genet*. 14: 269-276; Sanpei et al. (1996) *Nature Genet*. 14: 277-284; David et al. (1997) *Nature Genet*. 17: 65-70; Koob et al. (1998) *Nature Genet*. 18: 72-75. The substantial clinical variability among the remaining 40% of the genetically undefined dominant families suggests that a number of additional ataxia coding sequences remain to be identified. Suitable models are, for example the SCA7 murine model displaying neurodegeneration with progressive ataxin-7 accumulation (See e.g. Yvert et al. (2001) *Hum Mol Genet*. 10:1679-92), as well as in vitro systems as described in U.S. Pat. No. 5,834,183 to Orr et al.

(h) Spinal Muscular Atrophy

Spinomuscular atrophy (SMA) is a disease of the anterior horn cells of the spinal cord. There are several different types of SMA, including Type I or Acute (Severe) SMA, which is also known as Werdnig-Hoffmann Disease, Type II (Chronic) SMA, Type III (Mild) SMA, often referred to as Kugelberg-Welander or Juvenile SMA, Type IV (Adult Onset) SMA, and Adult Onset X-Linked SMA, also known as Kennedy's Syndrome or Bulbo-Spinal Muscular Atrophy, which occurs in males, but females may be carriers. SMA affects the voluntary muscles that are responsible for activities such as crawling, walking, head and neck control, and swallowing. SMA mainly affects the proximal muscles, or the muscles closes to the trunk of a person's body. Symptoms include weakness in the legs and arms, with weakness in the legs being greater than weakness in the arms. Other symptoms may include tongue fasciculations, or abnormal movements of the tongue. During the course of SMA, however, a person's senses, feelings and intellectual activity remain unaffected.

Suitable animal models of spinal muscular atrophy include, but are not limited to, the murine models described Fricker, (2000) *Drug Discovery Today* 5:220-221; Frugier, et al. (2000) *Human Molecular Genetics* 9:849-858; Hsieh-Li, et al. (2000) *Natural Genetics* 24:66-70; and Monani, et al. (2000) *Human Molecular Genetics* 9:333-339. In vitro systems of spinal muscular atrophy can be those described by Yoshida, et al. (1990) *J. Biol. Chem.* 265:17174-17179.

II. Proteasome Modulating Pharmacological Agent

In one aspect, the invention pertains to using proteasome modulators as pharmacological agents that modulate the proteasome, or a subunit of the proteasome. The terms "pharmacological agent" and "proteasome modulating pharmacological agent," as used herein, refer to the compound, or compounds, of the present invention that are used to modulate proteasome activity in a subject afflicted with a neurodegenerative disorder. Preferably, the proteasome modulating pharmacological agent of the present invention is a protease inhibitor. Suitable protease inhibitors include the protease inhibitors approved by the Food and Drug Administration and the protease inhibitors disclosed in Piccinini, et al. (2002) *AIDS*, 16: 693-700), the contents of which are herein incorporated in their entirety by reference. By way of non-limiting example, such protease inhibitors include lopinavir and its derivatives; nelfinavir and its derivatives; saquinavir and its derivatives; statine and its derivatives; amprenavir and its derivatives; indinavir and its derivatives; lasinavir and its derivatives; palinavir and its derivatives; tipranavir and its derivatives; (R)2QuinCOAsnPhe [CHOHCH$_2$]Pip-CONHtBu; 1-(2OHPr)-4-Substit-piperazine, thienyl carbarm ate and its derivatives; 1OH-2(Cbz-Tle)$_3$PhPr[14]paracyclophane and its derivatives; 1OH-2(Cbz-ValNH)$_3$PhPr[13]metacyclophane and its derivatives; 1OH-2(Cbz-ValNH)$_3$ PhPr[14]metacyclophane and its derivatives; 1OH-2(Cbz-ValNH)$_3$PhPr[17]metacyclophane and its derivatives; 2-Aminobenzylstatine Valyl Cbz and its derivatives; 2NaphCOAsnPhe[CHOHCH$_2$]Pro-OtBu and its derivatives; A-76890, A-77003; 2PyridCH$_2$NCH$_2$CO-Val-NHCH(Bz)] CHOHCHOH; A-77212; A-80987; A-81525; A-83962; A-98881; azacyclic urea and its derivatives; VX-478; 141W94; Ageneraseg®; BMS-186318; BILA 1906 BS; BILA 2185 BS; BocPhe[CHOH(CH$_2$)$_3$PHCO]IleAMBI; BzOCValPhe[diCHOH(RR)]PheValBzOC; BzOCValPhe[diCHOH(SS)]PheValBzOC; C2-Sym Phosphinic amide and its derivatives; CbzAF(CHOHCH$_2$)AVVOMe; CGP 53820; CGP 53820 and its analogs; bis-Val HOEt-N2 aza-peptide isotere; DMP-323; XM-323; DMP-450; Crixivan®; MK639; L-735,524; IsoquinCON furanyl urethane and its analogs; KNI-102; Cbz-Asn-Apns-Pro-NH-tBu; KNI-154; Noa-Asn-Apns-Thz-NH-tBu; KNI-174; Noa-Asn-Apns-Dmt-NH-tBu; KNI-227; Qoa-Mta-Apns-Thz-NH-tBu; KNI-272; iQoa-Mta-Apns-Thz-NH-tBu; L-685,434; L-685,434-6-Hydroxy and its derivatives; L-685,434-OEtNMe2; L-685,434-OPrMorph and its derivatives; L-687,908; BocPhe[CHOH(CH2)3CH=CHPhCO]IleAMBI; L-689,502; CGP 61755; ABT-378, ABT-578; Aluviran®; Kaletra; LY289612 and its analogs; LY314163; LY316957; AG1350; Nelfinavir-octahydro-thienopyridine and its analogs; LY326188; Thienopyrid-CON thienyl urethane and its derivatives; HOCH$_2$CH$_2$ isotere; Viracept®; AG-1343; P9941; BILA 2011 BS; Penicillin Et(NH)$_2$ Sym dimmer; Penicillin G, Et(NH)$_2$ and its derivatives; Penicillin 2Isoquin-OHPrNH$_2$ and its analogs; R-87366; AHPBA and its analogs; Ro 31-8959-bis-thf and its derivatives; Invirase®; Ro 31-8959; Fortovase®; (R)2QuinCOAsnPhe[CHOHCH2]PipCONHtBu; SB-205569; Val-Phe-Phe-HOCH2CH2 isotere and its analogs; SC-52151; SD146; Cyclic Urea Amide; SDZ PRI 053; ThienopyridCON thienyl urethane and its derivatives; U-140690; PNU-140690; Tle-Val-Sta, 5PhBuCOOH and its derivatives; Val-Val-Sta, 5PhBuCOOH and its derivatives; VB-11,328, and combinations thereof. The pharmacological agents of the present invention are also intended to include all chemical variants and analogs, as well as all chemical derivatives, of the protease inhibitors disclosed herein (See e.g., U.S. Pat. Nos. 5,916,438; 5,914,332; 6,147,095; 6,180,634; EP 0 708 085 and WO95/09843).

In one embodiment, the proteasome modulating pharmacological agent is a protease inhibitor that down-regulates the expression of a proteasome subunit (e.g., LMP-2, LMP-7 and MECL-1) by about 5-50% in the presence of the protease inhibitor compared with a control sample without the protease inhibitor. The expression of the proteasome subunit can be measured by examining a decrease in protein levels of the proteasome subunit, or by examining a decrease of RNA or DNA levels. Proteasome modulation can also be examined using the proteolysis assay described by Andre et al. (Andre et al. (1998) *Proc Natl Acad Sci U S A* 95:13120-4). In another embodiment, the proteasome modulating pharmacological agent up-regulates the expression of a proteasome subunit (e.g., LMP-2, LMP-7 and MECL-1) by about 5-50% in the presence of a protease activator compared with a control sample without the protease activator. The increased expression, or up-regulation of the proteasome subunit can be measured by examining an increase in protein levels of the proteasome subunit, or by examining a increase of RNA or DNA levels.

In a preferred embodiment, the proteasome modulating pharmacological agent is Ritonavir®, also known as Norvir®, which is chemically designated as 10-Hydroxy-2-methyl-5-(1-methylethyl)-4-thiazolyl]-3,6-dioxo-8,11-bis (phenylmethyl)-2,4,7,12-tetraazatridecan-13-oic acid, 5-thiazolylmethyl ester, [5S-(5R*,8R*,10R*,11R*)]. The chemical structure of this pharmacological agent is shown below:

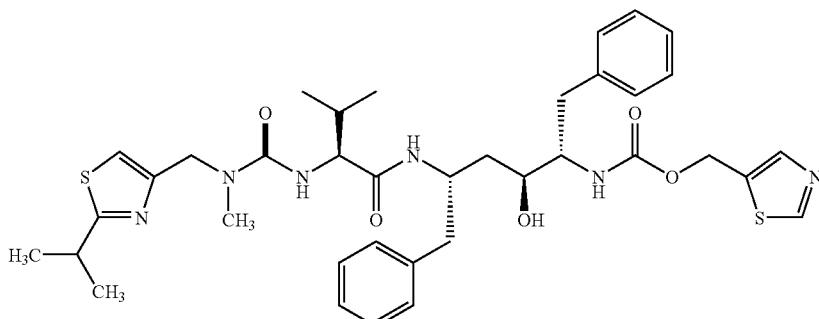

Other suitable pharmacological agents according to the present invention include analogs and chemical variants of the protease inhibitors disclosed herein. By way of non-limiting example, suitable analogs and chemical variants of the proteasome modulating pharmacological agents of the present invention include the compounds disclosed in U.S. Pat. Nos. 5,491,253 and 5,541,206, and in Kempf et al., (1995) *Proc. Natl. Acad. Sci. U.S.A.*, 92: 2484-2488 Piccinini, et al. (2002) *AIDS*, 16: 693-700, the contents of which are herein expressly incorporated in their entirety by reference. The term "pharmaceutical agent" is also intended to include all intermediate compounds and intermediate processes in the creation of a proteasome modulating pharmaceutical agent of the present invention.

The proteasome modulating pharmacological agents of the present invention are generally known as protease inhibitors. An exemplary pharmacological agent, Ritonavir®, has been approved by the FDA for use in anti-retroviral therapy in the treatment of Human Immunodeficiency Virus (HIV) infection. Proteases are enzymes that cleave proteins at specific peptide bonds. The genomes of retrovirus encode a protease that is responsible for the processing of various polyprotein precursors such as the gag and pol gene products, which are processed to form the viral core proteins and the HIV proteins reverse transcriptase, integrase and HIV protease, respectively. Correct processing of these polyprotein precursors is essential for the production of infectious virions. Protease inhibitors function by disabling the native protease enzyme, found within a host, before this enzyme can cleave the gag/pol polyprotein precursors to form the mature viral proteins. Protease inhibitors accomplish this inhibitory effect by a "lock and key" approach, meaning that the inhibitor fits within the binding site of an enzyme, thereby "locking up" the enzyme and rendering it ineffectual.

III. Proteasomes and Proteasome Modulation

While the pharmacological agent of the present invention is a known protease inhibitor, the present invention uses the pharmacological agent as a proteasome modulating drug in the treatment of neurodegenerative disorders.

(a) Proteasome Structure and Function

The proteasome is a multi-unit protein complex that plays a key role in protein degradation within a cell. The function of this key process ranges from ridding the cell of old and misfolded proteins to the degradation of key regulatory proteins and antigen generation for immune surveillance. In particular, proteolysis is involved in the regulation of numerous cellular processes including progression of the cell cycle, oncogenesis, transcription, development, growth and atrophy of developed tissues, flow of substrates through metabolic pathways, selective elimination of abnormal proteins and antigen processing (DeMartino, et al. (1999) *J. Biol. Chem.*, 274: 22123-126; Ottosen, et al. (2002) *Science*, 296: 479-81). The antigen-generating function of the proteasome allows targeted killing of defective and virally infected cells by the cytotoxic T-cells and natural killer cells.

The proteasome undergoes extensive modification to suit its different function. It does so by adding and replacing the individual subunits and by restructuring. At the core of all configurations is the 20S proteasome, which provides the proteasome its catalytic degradation power. 20S proteasomes are combined with various regulatory caps such as PA700 and PA28, which are thought to control the entry to 20S as well as the disposition of end products. The core of the 20S proteasome consists of two copies each of seven different $\alpha$ and $\beta$ subunits, which are arranged in four stacked rings ($\alpha_7\beta_7\beta_7\alpha_7$) (Verma et al. (2000) *Mol. Biol. Cell* 11: 3425-39). The interior of the ring structure contains a cavity consisting of three contiguous chambers joined by narrow constrictions (DeMartino, et al. (1999) *J. Biol. Chem.*, 274: 22123-126). The 7 beta subunits of the 20S proteasome provide the bulk of its peptide cleaving abilities. Three of these subunits, X ($\beta 5$), Y ($\beta 1$), and Z ($\beta 2$) can be replaced with inducible counterparts LMP2, LMP7, and MECL-1, which causes the proteasome to cleave peptides in a manner more specific for MHC I antigen presentation (Toes, et al. (2001) *J. Exp. Med.* 194: 1-12). These proteins are selectively induced under certain conditions, including treatment of cells with gamma-interferon. The LMP2, LMP7 and MECL-1 subunits assembly to form proteasomes with distinct subunit compositions and altered catalytic characteristics (DeMartino, et al. (1999) *J. Biol. Chem.*, 274: 22123-126). This configuration is known as the 'immunoproteasome' and is commonly presented in response to viral infection.

(b) Modulation of Proteasome Activity (1) Modulation of Normal Protein Degradation by the Proteasome Increasing evidence is accumulating that as a result of the normal aging process the body increasingly loses the ability to adequately degrade mutated or misfolded proteins. The proteasome is the cell machinery responsible for normal protein degradation. Oxidative stress is thought to contribute to this process of protein degradation through oxidation and nitration of intracellular proteins, which makes proteins prone to cross-linking and aggregation (Davies, (2001) *Biochimie*, 83(3-4): 301-10; Squier, (2001) *Exp. Gerontol.*, 36: 1539-50). Such aggregated proteins are more resistant to degradation in the proteasome and may cause inhibition of proteasomal function through irreversible binding to the proteasome (Davies, Supra; Squier, Supra). Alternatively or additionally, decreased proteasomal activity may be caused more directly by oxidation of the proteasome itself (Keller, et al. (2000) *Mech. Ageing Dev.* 113: 61-70). Aggregates of misfolded proteins can induce a number of changes in the proteasome that can lead to aberrant immune activation and apoptotic cell death. Age related loss of function or impediment of the proteasome is now thought to be at the heart of many neurodegenerative conditions such as Alzheimer's disease, Parkinson's disease, Huntington's disease, and ALS (Goldberg, et al. (2001) *Sci. Am.*, 284: 68-73; Johnston, et al. (2000) *Proc. Natl. Acad. Sci. U S A*, 97: 12571-76; Kopito, (2000) *Trends Cell. Biol.*, 10: 524-30).

(2) Modulation of Protein Degradation in Neurodegenerative Diseases

These same molecular mechanisms have been implicated in the pathogenesis of ALS, although there are qualitative or quantitative differences. Oxidative stress has been implicated as a contributing factor to the cause of ALS for more than a decade (See e.g., Cookson et al. (1999) *Brain Pathol*. 9:165-86; Cluskey et al. (2001) *Mol Pathol*. 54:386-92; and Beal (2002) *Free Radic Biol Med*. 32:797-803). Although oxidative stress may contribute to protein aggregation in sporadic ALS, in a qualitatively similar but quantitatively greater manner than in normal aging, recent evidence refutes the earlier implication that mutant superoxide dismutase-1 in familial ALS causes ALS by increasing oxidative stress; rather the current understanding is that the mutant gene causes a toxic function, which is likely to involve protein aggregation (Bruijn et al., (1998) *Science* 281(5384):1851-4.; Cleveland et al. (2000) *Nat Med*. 6:1320-1. Protein aggregation is also well recognized in sporadic ALS (Watanabe et al. (2001) *Neurobiol Dis*. 8:933-41). Protein aggregates co-localize with proteasomes in ALS (Watanabe et al. (2001) Supra). Inhibition of proteasomal activity increases abnormal protein accumulation, and accumulation of abnormal proteins contribute to inhibition of proteasomal activity Hoffman et al. (1996) *J Neurol Sci*. 139:15-20; and Watanabe et al. (2001) Supra). Proteasomal inhibition is a common feature in neurodegenerative diseases Ding et al. (2001) *Free Radic Biol Med*. 31:574-84. Activation of microglia is also a common feature of neurodegenerative diseases (See e.g., Hall et al. (1998) *Glia* 23:249-56; and McGeer et al. (1998) *Drugs* 55:739-46). Particularly in ALS, microglial activation increases as progression becomes more advanced and contributes to neuronal death through apoptosis (Hall et al. (1998) Supra and Alexianu et al. (2001) *Neurology*. 57:1282-9). Furthermore, the 20S proteasome is integral in processing abnormal proteins for antigen presentation in association with major histocompatibility complex 1 molecules on the surface of cells, which activates microglia Stohwasser et al. (2000) *Glia*. 29:355-65 and Groettrup et al. (2001) *Glia*. 29:355-65.

(3) Protein Misfolding, Aggregate Formation and Proteasome Dysfunction in Aggregate Diseases:

Cytosolic aggregates of proteins that stain for neurofilament, SOD and/or HSP along with proteasomal components are found in many sporadic and familial ALS spinal cords and also in Huntington's disease. Analysis of three lines of SOD1 mouse transgenics (G93A, G85R, and G37R SOD1) showed presence of cytosolic inclusions, which suggest that protein inclusions formation is a common event in ALS (Watanabe, et al. (2001) *Neurobiol. Dis*. 8: 933-41). It has been shown that formation of high molecular weight protein complexes is detected in the mSOD1 mice as early as day 30 and appears to be the earliest pathology detected in ALS currently.

More recently it has been shown that aggregate formation in Huntington disease model correlates with proteasomal dysfunction. Data from these studies indicate that poly-glutamine expression impairs proteasome activity and significantly blunts proteasome activity. Most interestingly cells expressing the poly-glutamine repeats showed altered expression of proteasomal subunits that belong to the immunoproteasome class. Expression of LMP2 was upregulated in cells harboring poly-glutamine repeats. This indicates that expression of poly-glutamine repeats mimics a stress response in these cells and alters the proteasome to an immunoproteasome form. Tissue specific proteasomal dysfunction is thought to play an important role in complex immune regulated diseases such as Graves disease and diabetes, etc. (Deng, et al. (1995) *Am. J. Hum. Genet*. 56: 528-34; Kuckelkorn, et al. (2002) *J. Exp. Med.*, 195: 983-90; Hayashi, etal. (2001)*J. Appl. Physiol*., 91: 2804-15).

(4) Immune Activation and Inflammation in ALS

Although ALS is not considered an autoimmune disease, recent studies implicate inflammation in disease pathogenesis. Activated microglia and expression of inflammatory mediators are observed in ALS spinal cord and a significant increase in free radical damage is seen in sera and CSF of ALS patients. In aging, microglia, the resident macrophages of the central nervous system are shown to become activated (Nichols, (1999) *J. Neurobiol.*, 40: 585-601; Yu, et al. (2002) *Neuroobiol. Aging*, 23: 105-15). Activation of microglia with aging both increases susceptibility to biochemical stress as well as to neurodegeneration (Nichols, Supra; Kullberg, et al. (2001) *Brain Res.*, 899(1-2): 169-86). Increased involvement of immune dysfunction in ALS patients is shown by higher incidence of autoimmune thyroid diseases (21%), paraproteinemias (5.6%), monoclonal immunoglobulin detection (60%), and co-association of lymphoma and MND (Gordon, et al. (1997) *Neurology*, 50: 576; Duarte, et al. (1991) *J. Neurol. Sci*. 104: 88-91; Shy, et al. (1986) *Neurology*, 36: 1429-1436; Sriram, et al. (1997) *Neurology*, 48: 464-70; Younger, et al. (1990) *Neurology*, 40: 595-599).

Studies by Gurney showed that the TgN (SOD1-G93A) G1H mice, an established animal model for ALS drug screening, showed significantly increased numbers of activated astrocytes (P<0.01) at 100 days of age in both the cervical and lumbar spinal cord regions (Hall, et al. (1998) *Glia*, 23: 249-256). However, at 120 days of age, the activation lost statistical significance. In contrast, microglial activation was significantly increased several-fold at both 100 and 120 days. Gene expression analysis of post mortem ALS spinal cord demonstrated significant increase in macrophage/microglial activation markers as compared to normal and other disease controls (Malaspina et al. (2001) *J. Neurochem.*, 77: 132-45). In addition recent studies based on Gene expression analysis of mSOD1 mouse spinal cord at various stages of ALS demonstrated the presence of activated microglial signature well before clinical changes (70 days) suggesting that microglial activation occur prior to neuronal damage (Olsen, et al. (2001) *Ann. Neurol.*, 50: 730-40).

Proteasomal dysfunction can play an important role in the inflammatory process through modulation of key inflammatory mediators such as Jak3 kinase and IkappaB (Kwon, et al. (1998) *Diabetes*, 47: 583-91; Rivett, et al. (2000) *J. Pept. Sci.*, 6: 478-88; Yu, et al. (1997) *J. Biol. Chem*. 272: 14017-20). Additionally alteration in proteasome from constitutive to inducible form can enhance immune monitoring by cytotoxic T-cells and NK cells that can recognize the antigen generated by the dysfunctional proteasome as foreign and lead to elimination of defective cells by apoptosis. This process can lead to inflammation and microglial activation by elaborating cytokines such as TNF-alpha and IFN-gamma that can perpetuate this continuous cycle.

Accordingly, proteasomal dysfunction can alter the progression of diseases such as ALS by a variety of ways. It is believed that proteasome alteration in ALS modulates important factors involved in cell cycle regulation, apoptosis, inflammation, and antigen presentation, which individually or in combination can lead to disease propagation. Proteasome modifying drugs that can reverse the dysfunction have great potential in the treatment of ALS and neurodegeneration produced by intracellular protein aggregates.

(5) Modulating Proteasome Activity by the Pharmacological Agent

The present invention uses the pharmacological agent as a proteasome modulating drug. The pharmacological agent was selected as a candidate for a proteasome modulating drug in vivo screening program by searching for an FDA approved drug which would modulate the proteasome's ability to process and present antigen (Andre, et al. (1998) *Proc. Natl. Acad. Sci. USA*, 95: 13120-24). In previous animal efficacy studies, the pharmacological agent, which has been shown to attenuate MHC I antigen presentation through modulation of LMP7, prevented the development of experimental autoimmune encephalomyelitis (EAE), which is an immune-mediated central nervous system disease that is thought to model multiple sclerosis (Andre, et al., Supra; Hosseini, et al. (2001) *J. Neuroimmunol.*, 118: 233-44).

Mechanistic action of the pharmacological agent on the proteasome is thought to be mediated by blocking the covalent modification of the binding site for the immunoproteasome subunit LMP7. This process leads to alteration of peptides generated by the proteasome (Schmidtke, et al. (1999) *J. Biol. Chem*. 274: 35734-40). The proteasome is involved in generation of antigens for the MHC class I molecules. Another AIDS protease saquinavir also alters proteasome activity but does so at very high concentrations. The pharmacological agent's proteasomal action can be mediated at therapeutic doses used in the treatment of AIDS and may be clinically useful in the treatment of ALS (Denissen, et al. (1997) *Drug Metab. Dispos*. 25: 489-501). At high doses (approximately 100 µM) the pharmacological agent can also inhibit IκB degradation and NF-κB mediated signal transduction that may lead to inflammation (Schmidtke, et al. Supra).

The proteasome enzyme is "multicatalytic," i.e. it has at least three distinctly different catalytic sites including: (i) a peptidylglutamyl-peptide hydrolyzing site, which cleaves peptides with glutamic acid in the P1 position (e.g. CBZ-Leu-Leu-Glu-X); (ii) a "trypsin-like" site, which cleaves peptides with basic amino acids in the P1 position (e.g. CBZ-Val-Leu-Arg-X); and (iii) a "chymotrypsin-like" site, which cleaves peptides with leucine or other hydrophobic amino acids in the P1 position (e.g. CBZ-Gly-Gly-Leu-X). Two other activities have also been associated with the proteasome, one exhibiting a preference for cleavage of peptide bonds on the carboxyl side of branched chain amino acids and the other toward bonds between small neutral amino acids. (Orlowski, (1990) *Biochemistry* 29: 10289-10297).

Various inhibitors of the peptidases of the proteasome have been reported (See e.g., U.S. Pat. Nos. 6,117,887, 6,075,150, 5,693,617, 5,847,076, Dick, et al, (1991) *Biochemistry* 30:2725-2734; Goldberg, et al., (1992) *Nature* 357:375-379; Goldberg, (1992) *Eur. J. Biochem*. 203:9-23; Orlowski, Supra; Rivett et al. (1989) *Archs. Biochem. Biophys*. 218:1; Rivett, et al. (1989) *J. Biol. Chem*. 264:12,215-12,219; Tanaka et al. (1992) *New Biol*. 4:1-11). These include known inhibitors of chymotrypsin-like and trypsin-like proteases, as well as inhibitors of thiol (or cysteine) and serine proteases. Examples of peptide aldehydes that have been reported to inhibit the chymotrypsin-like activity are described by Vinitsky, et al (1992) *Biochemistry* 31:9421-9428; Tsubuki, et al. (1993) *Biochem. Biophys. Res. Commun*. 196:1195-1201; and Rock et al. (1994) *Cell* 78:761-771). These include the N-acetyl-L-leucinyl-L-leucinal-L-norleucinal (ALLN) compounds and closely related compounds, N-acetyl-L-leucinyl-L-leucinyl-methional (LLM), N-carbobenzoxyl-L-leucinyl-L-leucinyl-L-norvalinal (MG 115). Other inhibitors of the chymotrypsin-like activity of the proteasome include a series of potent dipeptide inhibitors (Iqbal, et al (1995) *J. Med. Chem*. 38:2276-2277) and a series of similarly potent inhibitors from α-ketocarbonyl and boronic ester derived dipeptides (Iqbal, et al. (1996) *Bioorg. Med. Chem. Lett* 6:287-290). Of the several peptide α-keto ester inhibitors tested, Z-Leu-Leu-Phe-COOEt was the most potent inhibitor of the chymotrypsin-like activity. The inhibitors may also be stable analogs of catalytic transition states (transition state analog inhibitors), such as Z-glycine-glycine-leucine-H, which inhibits the chymotrypsin-like activity of the proteasome (Orlowski, (1990) Supra; see also Kennedy et al. (1979) *Biochemistry* 18:349).

Other tripeptides that have been described in the literature include Ac-Leu-Leu-Leu-H, Ac-Leu-Leu-Met-OR, Ac-Leu-Leu-Nle-OR, Ac-Leu-Leu-Leu-OR, Ac-Leu-Leu-Arg-H, Z-Leu-Leu-Leu-H, Z-Arg-Leu-Phe-H, and Z-Arg-Ile-Phe-H, where OR, along with the carbonyl of the preceding amino acid residue, represents an ester group.

Various natural and chemical protease inhibitors reported in the literature, or molecules similar to them, include peptides containing an α-diketone or an α-keto ester, peptide chloromethyl ketones, isocoumarins, peptide sulfonyl fluorides, peptidyl boronates, peptide epoxides, and peptidyl diazomethanes (Angelastro et al. (1990) *J. Med. Chem*. 33:11-13; Bey et al., EPO 363,284; Bey et al., EPO 364,344; Grubb et al., WO 88/10266; Higuchi et al., EPO 393,457; Ewoldt et al. (1992) *Mol. Immunol*. 29:713-721; Hernandez et al. (1992) *J. Med. Chem*. 35: 1121-1129; Vlasak et al. (1989) *J. Virol*. 63:2056-2062; Hudig et al. (1991) *J. Immunol*. 147: 1360-1368; Odakc et al. (1991) *Biochemistry* 30:2217-2227; Vijayalakshmi et al. (1991) *Biochemistry* 30:2175-2183; Kam et al. (1990) *Thrombosis and Haemostasis* 64:133-137; Powers et al. (1989) *J. Cell. Biochem*. 39:33-46; Powers et al. Proteinase Inhibitors, Barrett et al., Eds., Elsevier, pp. 55-152 (1986); Powers et al., (1990) *Biochemistry* 29:3108-3118; Oweida et al., (1990) *Thrombosis Research* 58:391-397; Hudig et al., (1989) *Mol. Immunol*. 26:793-798; Orlowski et al. (1989) *Arch. Biochem. Biophys*. 269:125-136; Zunino et al. (1988) *Biochemimica et Biophysica Acta*. 967:331-340; Kam et al. (1988) *Biochememistry* 27:2547-2557; Parkes et al. (1985) *Biochemem J*. 230:509-516; Green et al. (1981) *J. Biol. Chem*. 256:1923-1928; Angliker et al., (1987) *Biochemem. J*. 241:871-875; Puri et al. (1989) *Arch. Biochem. Biophys*. 27:346-358; Hanada et al. Proteinase Inhibitors: Medical and Biological Aspects, Katunuma et al., Eds., Springer-Verlag pp. 25-36 (1983); Kajiwara et al. (1987) *Biochemem. Int*. 15:935-944; Rao et al. (1987) *Thrommb. Res*. 47:635-637; Tsujinaka et al. (1988) *Biochemem. Biophys. Res. Commun*. 153:1201-1208).

Siman et al. (WO 91/13904) disclose chymotrypsin-like proteases and their inhibitors. The inhibitors have the formula:

R-A4-A3-A2-Y, wherein

R is hydrogen, or a N-terminal blocking group;

A4 is a covalent bond, an amino acid or a peptide;

A3 is a covalent bond, a D-amino acid, Phe, Tyr, Val, or a conservative amino acid substituent of Val;

A2 is a hydrophobic amino acid or lysine or a conservative amino acid substituent thereof, or when A4 includes at least two amino acids, A2 is any amino acid; and Y is a group reactive with the active site of said protease.

Powers (WO 92/12140) discloses peptide ketoamides, ketoacids, and ketoesters and their use in inhibiting serine proteases and cysteine proteases.

IV. Treatment of Neurodegenerative Disorders Using Proteasome Modulating Drugs (a) In Vivo Model for the Study and Treatment of Neurodegenerative Disorders Using the Proteasome Modulating Pharmacological Agent The FDA approved AIDS drug Ritonavir® (Norvir®), has a specific effect on the proteasome that is relevant to the deleterious changes in ALS. Although much basic animal and cell culture research has been performed on the role of the proteasome in the neurodegenerative diseases, modulation of this mechanism has not been the target of a clinical investigation in ALS or any other neurodegenerative disease. Compelling data from laboratory cell culture experiments and an animal study using a mouse model of ALS indicates that this approach holds great promise. Success in this endeavor will be immediately meaningful for ALS patients as well as for the broader realms of neurodegenerative disease research and research into other diseases whose causes are associated with the aging process.

The SOD1 G93A (high copy) mouse model for ALS is a suitable mouse that carries 25 copies of the human G93A SOD mutation and is driven by the endogenous promoter. Survival in the mouse is copy dependent. The high copy G93A has a median survival of around 128 days. High molecular weight complexes of mutant SOD protein are seen in the spinal cord beginning around day 30. At day 60 reactive astrocytosis (GFAP reactive) are observed; activated microglia are observed from day 90 onwards. Studies by Gurney et al. showed that at day 90 reactive astrocytosis loses statistical significance while microglial activation is significantly elevated and continues to be elevated through the end stage of the disease (See Gurney, et al. (1996) *Ann. Neurol.*, 39: 147-5739).

Many drugs that have shown efficacy in this model have moved forward into human clinical trials. Experience with riluzole, the only approved drug in the treatment of ALS, indicates that the mouse ALS model is a good predictor of clinical efficacy. Other drugs such as Creatine, Celebrex, Co-enzyme Q10, and Minocycline are under clinical evaluation based on studies in this model.

(b) Delivery of the Proteasome Modulating Pharmacological Agent in the Treatment of Neurodegenerative Disorders The pharmacological agent of the present invention can be incorporated into pharmaceutical compositions suitable for administration to a subject. Typically, the pharmaceutical composition comprises a proteasome modulating pharmacological agent of the present invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

The pharmaceutical compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. The preferred mode of administration is parenteral (e.g., intravenous, subcutaneous, intraperitoneal, intramuscular). In a preferred embodiment, the pharmacological agent is administered by an intraperitoneal injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., the pharmacological agent) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The proteasome modulating pharmacological agent of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g., *Sustained and Controlled Release Drug Delivery Systems*, J. R. Robinson, ed., Marcel Dekker, Inc., New York, 1978; U.S. Pat. Nos. 6,333,051 to Kabanov et al., and 6,387,406 to Kabanov et al.).

In certain embodiments, a proteasome modulating pharmacological agent of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In certain embodiments, a proteasome modulating pharmacological agent of the present invention can be administered in a liquid form. The pharmacological agent of the present invention is freely soluble in a variety of solvents, such as for example, methanol, ethanol, and isopropanol. The pharmacological agent is, however, highly lipophilic and, therefore, substantially insoluble in water. A variety of methods are known in the art to improve the solubility of the pharmacological agent in water and other aqueous solutions. For example, U.S. Pat. No. 6,008,192 to Al-Razzak et al. teaches a hydrophilic binary system comprising a hydrophilic phase and a surfactant, or mixture of surfactants, for improving the administration of lipophilic compounds such as the pharmacological agent of the present invention.

Supplementary active compounds can also be incorporated into the compositions. In certain embodiments, a proteasome modulating pharmacological agent of the invention is coformulated with and/or coadministered with one or more additional therapeutic agents that are useful for improving the pharmacokinetics of the pharmacological agent. A variety of methods are known in the art to improve the pharmacokinetics of the pharmacological agent of the present invention. For example, U.S. Pat. No. 6,037,157 to Norbeck et al. discloses a method for improving the pharmacokinetics of the pharmacological agent by coadministration of the pharmacological agent and a drug that is metabolized by the cytochrome P450 monooxygenase, such as for example, the P450 3A4 isozyme. According to the teachings of this patent, some drugs, particularly HIV protease inhibitors, are metabolize by the cytochrome P450 monooxygenase, which results in unfavorable pharmacokinetics and the need for more frequent and/or higher doses of the pharmacological agent. Thus, co-administration of an additional agent that inhibits metabolism by cytochrome P450 monooxygenase will improve the pharmacokinetics of the pharmacological agent of the present invention.

Other methods of improving the pharmacokinetics of the pharmacological agent have been disclosed, for example, in U.S. Pat. No. 6,342,250 to Masters, U.S. Pat. No. 6,333,051 to Kabanov et al., U.S. Pat. No. 6,395,300 to Straub et al., U.S. Pat. No. 6,387,406 to Kabanov et al., and U.S. Pat. No. 6,299,900 to Reed et al. Masters discloses a drug delivery device and method for the controlled release of pharmacologically active agents including the pharmacological agent of the present invention. The drug delivery device disclosed by Masters is a film comprising one or more biodegradable polymeric materials, one or more biocompatible solvents, and one or more pharmacologically active agents dispersed uniformed throughout the film. In U.S. Pat. No. 6,333,051, Kabanov et al. disclose a copolymer networking having at least one cross-linked polyamine polymer fragment, at least one nonionic water-soluble polymer fragment, and at least one suitable biological agent, including the pharmacological agent of the present invention. According to the teachings of this patent, this network, referred to as a nanogel network, improves the therapeutic effect of the pharmacological agent by decreasing side effects and increasing therapeutic action. In another patent, U.S. Pat. No. 6,387,406, Kabanov et al. also disclose another composition for improving the oral delivery of numerous pharmacological agents, including the pharmacological agent of the present invention. This delivery vehicle comprises a biological agent and a poly(oxyehtylene)-poly(oxypropylene) block copolymer. Straub et al. Supra disclose porous drug matrices for use with drugs, and in particular, for use with low-aqueous solubility drugs, for enhancing solubility of the drug in an aqueous solution. Reed et al. Supra disclose a drug delivery system, which uses a dermal penetration enhancer to transport a variety of physiologically active agents, including the pharmacological agent of the present invention, across a dermal surface or mucosal membrane of a subject.

Other methods for improving the delivery and administration of the pharmacological agent of the present invention include means for improving the ability of the pharmacological agent to cross membranes, and in particular, to cross the blood-brain barrier. In one embodiment, the pharmacological agent can be modified to improve its ability to cross the blood-brain barrier, and in an alternative embodiment, the pharmacological agent can be co-administered with an additional agent, such as for example, an anti-fungal compound, that improves the ability of the pharmacological agent to cross the blood-brain barrier. Alternatively, precise delivery of the pharmacological agent into specific sites of the brain, can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for pharmacological agent microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The pharmacological agent can be delivered to regions, such as the cells of the spinal cord, brainstem, or brain that are associated with the disease or disorder. For example, target regions can include the medulla, pons, and midbrain, cerebellum, diencephalon (e.g., thalamus, hypothalamus), telencephalon (e.g., corpus stratium, cerebral cortex, or within the cortex, the occipital, temporal, parietal or frontal lobes), or combinations, thereof.

Proteasome modulating pharmacological agents of the present invention can be used alone or in combination to treat neurodegenerative disorders. For example, the pharmacological agent can be used in conjunction with other existing HIV protease inhibitors, for example, to produce a synergistic effect. Likewise, the pharmacological agent can be used alone or in combination with an additional agent, e.g., an agent which imparts a beneficial attribute to the therapeutic composition, e.g., an agent which effects the viscosity of the composition. The combination can also include more than one additional agent, e.g., two or three additional agents if the combination is such that the formed composition can perform its intended function.

The pharmaceutical compositions of the invention may include a "therapeutically effective amount" or a "prophylactically effective amount" of a pharmacological agent of the invention. A "therapeutically effective amount" refers to an amount effective, at dosages and for periods of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a pharmacological agent (e.g., Ritonavir®) of the invention is between 50 mg/day to about 2000 mg/day administered to a subject, or group of subjects, preferably about 100 mg/day to about 1500 mg/day, more preferably about 100 mg/day to about 1200 mg/day, and most preferably about 300 mg/day to 400 mg/day. Preferably, administration of a therapeutically effective amount of pharmacological agent (e.g., Ritonavir®), results in a concentration of pharmacological agent in the bloodstream in the range of 1 nanomolar (nM) to 100 millimolar (mM) concentration. For example, a concentration range of about 10 nM to about 10 mM, about, 1 nM to about 1 mM, about 1 mM to about 100 micromolar ($\mu$M), about 1 $\mu$M to about 500 $\mu$M, about 1 $\mu$M to about 200 $\mu$M, preferably about 10 $\mu$M to about 50 $\mu$M. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

(c) In Vitro Analysis of Modulation of Proteasome Activity in Neurodegenerative Disorders (i) Protein Aggregation Induces Changes in Proteasome Function and Alters Antigen Presentation An immunoproteasome is formed when constitutive expression of subunits X, Y and Z are replaced by the inducible subunits LMP-2, LMP-7 and MECL-1, which make them specialized for MHC-Class I presentation. A series of experiments have been conducted to establish whether or not the presence of a mutant protein, such as those found in ALS or Huntington's, would produce any alteration in proteasome function and alter antigen presentation by Major Histocompatibility Antigen Class I molecules (MHC Class I). These studies investigated the expression of MHC-class I molecules on surface of cells carrying normal 19 glutamine repeats and compared them to cells carrying the pathological 56 glutamine repeats, as well as wild-type versus mSOD-containing cells. Additionally this study also analyzed if individual proteasomal subunits were altered in ALS.

As a result of these studies, it has been determined that expression of MHC-class I was reduced by 10-20% on cells carrying 56 polyglutamine repeats. Analysis of murine cells carrying the mutant SOD gene also showed a greater reduction in MHC class I expression. Cells carrying the mutant SOD gene showed a 79% decrease on surface expression of MHC class I $H2D^k$ as compared to normal N2A cells. To corroborate the alteration in MHC class I to antigen processing in the proteasome the expression of two critical subunits of the immunoproteasome was investigated. Northern analysis of normal and SOD1 G85R expressing cells showed that expression of basal levels of LMP-2, LMP-7 and MECL-1 is high in mSOD cells. Stimulation of cellular stress response by heat shock increased the expression of LMP-2, LMP-7 and MECL-1 (FIGS. 1 and 2). These findings implicate the involvement of immunoproteasome in ALS pathogenesis and that proteasome-modifying drugs show promise in ALS therapy.

V. Screening Assay for Proteasome Modulating Pharmacological Agents

The methods of the invention can be used to screen a large number of candidate compositions to find pharmacological agents capable of modulating proteasome activity in a subject. The screening assay methods of the present invention are preferably cellular assays that include a cell line that can be stably cultured using standard cell culture techniques known to those having ordinary skill in the art. For example, the screening assay methods of the present invention can include the steps of (i) determining the level of proteasome activity in a substrate, (ii) applying a pharmacological agent to the substrate, and (iii) measuring changes in the level of proteasome activity in response to the applied pharmacological agent.

The screening assay method of the present invention can be run under normal conditions, or alternatively, the screening assay can be run in the presence various stress models. Preferable stress models include, but are not limited to, heat shock models and oxidative stress models. According to the present invention, the stress models can be introduced either before or after the application of a pharmacological agent to the substrate.

VI. Predictive and Diagnostic Medicine

The present invention also pertains to the field of predictive medicine in which a variety of assays, including, but not limited to diagnostic assays, prognostic assays, and monitoring assays are used for prognostic (predictive) purposes to thereby treat an individual prophylactically. Accordingly, one aspect of the present invention relates to diagnostic assays for comparing proteasome activity in a control biological sample (e.g., blood, serum, cells, tissue) with the proteasome activity of a test biological sample (e.g., blood, serum, cells, tissue) to thereby determine whether an individual is afflicted with a neurodegenerative disease or disorder, or is at risk of developing a neurodegenerative disorder, which is associated with decreased proteasome activity. The invention also provides for prognostic (or predictive) assays for determining whether an individual is at risk of developing a neurodegenerative disorder associated with decreased proteasome activity. For example, the proteasome activity level can be assayed in a biological sample. Such assays can be used for prognostic or predictive purposes to thereby phophylactically treat an individual prior to the onset of a neurodegenerative disorder (e.g., ALS, Parkinson's disease, Huntington's disease, and Alzheimer's disease) characterized by or associated with decreased proteasome activity.

These assays are described in further detail in the following sections.

1. Diagnostic Assays

An exemplary method for diagnosing whether a subject is afflicted with a neurodegenerative disease involves the steps of (i) obtaining a control biological sample (e.g., non-neurodegenerative disorder sample) from a control subject, (ii) obtaining a test biological sample from a test subject, (iii) detecting the respective levels of proteasome activity in the control sample and the test sample, and (iv) comparing the respective levels of proteasome activity in the control sample and the test sample.

Biological samples (e.g., blood, serum, cells, tissue) can be obtained from a subject using a variety of methods known to those having ordinary skill in the art. By way of non-limiting example, tissue samples can be removed from a subject using surgical methods such as biopsy, while blood samples can be taken from a subject using standard blood-drawing techniques. Serum and cell samples can be obtained, for example, by processing blood samples taken from a subject.

In another embodiment, the methods for determining whether a subject is afflicted with a neurodegenerative disease involves determining the effect of a pharmacological agent on a test sample by (i) obtaining a biological sample from a test subject, (ii) detecting a level of proteasome activity in the sample, (iii) applying a pharmacological agent to the biological sample, and (iv) measuring changes in the level of proteasome activity in response to the applied pharmacological agent.

In yet another embodiment, the methods for determining whether a subject is afflicted with a neurodegenerative disease involves the steps of (i) obtaining a control biological sample (e.g., non-neurodegenerative disorder sample) from a control subject, (ii) obtaining a test biological sample from a test subject, (iii) detecting the respective levels of proteasome activity in the control sample and the test biological sample, (iv) applying a pharmacological agent to the test biological sample, (v) determining the level of proteasome activity in the test biological sample in response to the applied pharmacological agent and (vi) comparing the level of proteasome activity in the test sample, as determined in step (v), with the level of proteasome activity of the control sample, as determined in step (i).

The invention also encompasses kits for assessing and monitoring the proteasome activity level of proteasome activity in a biological sample. For example, the kit can comprise means for determining the level of proteasome activity in the sample; and means for comparing the level of proteasome activity in the sample with a standard, or control level, of proteasome activity. The kit can further comprise instructions for using the kit to detect level of proteasome activity in a sample.

2. Prognostic Assays

The diagnostic methods described herein can furthermore be utilized to identify subjects having, or at risk of developing, a neurodegenerative disease or disorder associated with aberrant levels of proteasome activity. As used herein, the term "aberrant" includes a level of proteasome activity which deviates from the wild type level of proteasome activity. Aberrant proteasome activity includes increased or decreased proteasome activity.

The assays described herein, such as the preceding diagnostic assays or the following assays, can be utilized to identify a subject having, or at risk of, developing a neurodegenerative disorder associated with a change in proteasome activity, such as for example ALS, Parkinson's disease, Huntington's disease and Alzheimer's disease. Thus, the present invention provides a method for identifying a neurodegenerative disease or disorder associated with aberrant proteasome activity in which a test sample is obtained from a subject and level of proteasome activity is detected and compared to the level of proteasome activity in a control sample, thereby determining whether the proteasome activity of the test sample is aberrant, wherein the detection of aberrant level of proteasome activity is diagnostic for a subject having or at risk of developing a neurodegenerative disease or disorder associated with aberrant proteasome activity.

Furthermore, the prognostic assays described herein can be used to determine whether a subject can be administered a pharmacological agent, and, optionally, other therapeutic agent (e.g., an agonist, antagonist, peptidomimetic, protein, peptide, nucleic acid, small molecule, or other drug candidate) to treat a disease or disorder associated with increased or decreased level of proteasome activity. For example, such methods can be used to determine whether a subject can be effectively treated with an agent for a neurodegenerative disorder such as ALS, Parkinson's disease, Huntington's disease and Alzheimer's disease. Thus, the present invention provides methods for determining whether a subject can be effectively treated with a pharmacological agent for a neurodegenerative disorder associated with increased or decreased level of proteasome activity in which a test sample is obtained and the level of proteasome activity is detected (e.g., wherein significant change in the level of proteasome activity is diagnostic for a subject that can be administered the pharmacological agent to treat a neurodegenerative disorder associated with increased or decreased level of proteasome activity).

3. Monitoring the Effects of Pharmacological Agent

Monitoring the influence of the pharmacological agents of the present invention on the level of proteasome activity can be applied not only in basic drug screening, but also in an on-going evaluation of the continued effectiveness of the pharmacological assays of the present invention. According to this aspect of the present invention, methods for determining the continued effectiveness of a pharmacological agent involve the steps of: (i) obtaining a biological sample from a test subject at a first point in time, (ii) detecting a level of proteasome activity in the sample at a first point in time, (iii) applying a pharmacological agent to the biological sample, (iv) measuring changes in the level of proteasome activity in response to the applied pharmacological agent at a first point in time, (v) repeating steps (i) through (iv) for n number of times, where n can be virtually any number of repetitions, and (vi) comparing the changes in the level of proteasome activity for each time point.

Equivalents

Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims. All publications and references are herein expressly incorporated in their entirety by reference in their entirety.

EXAMPLES

The following examples merely illustrate that one pharmacological agent according the present invention, the HIV protease inhibitor Ritonavir®, delays neurodegenerative disease progression and prolongs the life of male SOD1 G93A mice. However, these examples are merely illustrative of the present invention and are not designed to limit the scope of this invention.

Example 1

Methods and Materials

Model Description: The SOD1 G93A (high copy) mouse model is a mouse that carries 25 copies of the human G93A SOD mutation and is driven by the endogenous promoter. Survival in the mouse is copy dependent. The high copy G93A has a median survival of around 128 days. High molecular weight complexes of mutant SOD protein are seen in the spinal cord beginning around day 30. At day 60 reactive astrocytosis (GFAP reactive) are observed; activated microglia are observed from day 90 onwards. Studies by Gurney et al. (Supra) showed that at day 90 reactive astrocytosis loses statistical significance while microglial activation is significantly elevated and continues to be elevated through the end stage of the disease (See Gurney, et al. (1996) *Ann. Neurol.*, 39: 147-5739).

Many drugs that have shown efficacy in this model have move forward into human clinical trials. Experience with riluzole, the only approved drug in the treatment of ALS, indicates that the mouse ALS model is a good predictor of clinical efficacy. Other drugs such as Creatine, Celebrex, Co-enzyme Q10 are under clinical evaluation based on studies in this model.

Materials: Oral formulation of Ritonavir® was purchased using research protocol from Cardinal Health Care. Riluzole was purchased from Sigma.

Murine ALS model: Heterozygous transgenic mice carrying the human SOD-1 (G93A) gene were obtained from Jackson Laboratory (Bar Harbor, Me., USA) and experiments were performed under IRB protocol at Massachusetts College of Pharmacy.

Methods: The study consisted of a treatment group of 20 SOD G93A mice, an SOD G93A control group of 20 mice receiving treatment with riluzole, and two SOD G93A vehicle control groups of 20 mice each.

Control Drug: Riluzole: 20 mg/Kg/day in drinking water
Proteasome Modulating Pharmacological Agent: Ritonavir®: 50 mg/Kg/day IP injection Control Drug and Pharmacological Agent Preparation and Delivery: The drugs were formulated in suitable vehicles and control groups were given the same vehicle as treatment. Riluzole was administered according to protocol by Gurney et al. (Gurney, et al. (1996) *Ann. Neurol.*, 39: 147-5739). Ritonavir® treatment was administered by IP bolus injections once daily 5 d/wk. Ritonavir® dosage was based on the EAE model where it was protective and showed inhibition of proteasomal chymotrypsin activity at 5 uM concentration (Hosseini, et al. (2001) *J. Neuroimmunol.* 118: 233-44.36). Mice were treated from 60 days of age until death and were monitored daily for weight, neurological score and death.

Neurological Scoring: From day 85 onward, neurological score was recorded on a 4-point scale:
  0=Normal reflex on the hind limbs (animal will splay its hind limbs when lifted by its tail)
  1=Abnormal reflex (Lack of splaying of hind limbs when animal is lifted by the tail).
  2=Abnormal reflex and visible evidence of paralysis
  3=Lack of reflex and total paralysis of hind limbs.
  4=Inability to right themselves when placed on the sides in 30 seconds or found dead. The animals are sacrificed at this stage if alive.

Statistical Analysis: Statistical analysis on the neurological score, body weight and survival was done by utilizing ANOVA, Kaplan Meier, t-test, Cox's proportional hazards regression model and mixed linear model methods. All statistical analysis was performed using standard procedures known in the art.

Example 2

Modulation of ALS in a SOD-1 (G93A) Mouse Model

This example demonstrates the effects of Ritonavir® (an approved HIV protease-inhibiting drug) that binds to the LMP7 component of the immunoproteosome, resulting in decreased antigen processing and MHC I expression. It has also been shown to inhibit the activity of caspase 3 (a mediator of programmed cell death, or apoptosis) and to suppress cell proliferation by arresting cells in the GI phase the cell cycle (See e.g., Pati et al. (2002) *Blood*, 99: 3771-3779). The positive control drug in this model was riluzole (Rilutek®), the FDA approved drug for ALS. Various dosing paradigms were investigated to optimize the effect of Ritonavir®. Once the optimum paradigm was established, three separate studies employing similar dosing paradigms were conducted. The results from all three experiments support the conclusion that Ritonavir® is more active than the positive control riluzole (Rilutek®) in this model. This conclusion is based on analysis of both neurological score data (which reflects disease progression through assessment of hindlimb motor dysfunction and paralysis) and of survival data.

The results of the study are summarized in FIGS. 3-14 and Tables 1 and 2. Given the separate statistical analysis of the sources of variation in the model, the most reliable information comes from litter matched data sets. Across studies, this amounts to 48 untreated+48 treated litter matched animals in the case of Ritonavir® and 33+33 for Riluzole. Analysis of such cross-study litter matched data for each drug shows that while riluzole had no significant effect on slowing disease progression (neurological score), Ritonavir's effect was highly significant ($p<0.0001$). The two drugs showed equal effects on survival prolongation when both genders were included in the analysis (2%). However, both drugs showed a gender bias in their effects, with Riluzole showing an maximum overall efficacy of 3% (in females, not statistically significant) and Ritonavir® of 6% (in males, nearly significant with $p<0.06$) (See Table 1). (Note: The efficacy gender bias towards males exhibited by Ritonavir® occurred in the face of a survival bias (4%) towards females in the model generally, an effect also observed in the untreated, littermatched controls in the Ritonavir® studies (3%) (See Table 2). This underscores the reliability of the Ritonavir® data set and makes the drug's efficacy in males more reliable).

Abbott (the developer of Ritonavir®) has shown that the drug reaches higher plasma levels in female animals as compared to males, and this may account for the apparent gender bias in its efficacy. The dose of Ritonavi® in these studies (50 mg/Kg) is quite close to its maximal tolerated dose. It is possible that the higher drug exposure in females resulted in a higher degree of toxicity which may have limited the expression of drug efficacy relative to males.

Further pre-clinical studies may help to identify the specific mechanism of Ritonavir®'s efficacy in the ALS mouse model (e.g. inhibition of cell proliferation, of protease/proteosome activity, of antigen presentation, etc.) enabling development of more efficacious and safer (i.e. more specifically targeted) second and third generation drugs.

TABLE 1

Summarized data from ALS-TDF Ritonavir ® and Riluzole studies

| Study | N/Group | Combined (Days) (% effect on survival@) | Male (Days) (% effect on survival@) | Female (Days) (% effect on survival@) | Neurological score significance (Males & Females combined)¶ |
|---|---|---|---|---|---|
| Ritonavir-1 | Control = 20 | 139 | 135 | 142 | p < 0.0001 |
|  | Treated = 20 | 145 | 149 | 141 |  |
|  |  | 5% | 10% | None |  |
| Ritonavir-2 | Control = 18 | 139 | 142 | 136 | p < 0.0001 |
|  | Treated = 18 | 149 | 153 | 144 |  |
|  |  | 7% | 8% | 6% |  |
| Ritonavir-3 | Control = 18 | 135 | 130 | 141 | p = 0.0007 |
|  | Treated = 18 | 137 | 139 | 134 |  |
|  |  | 2% | 7% | −5% |  |
| Combined Ritonavir (100% Litter matched)** | Control = 48 | 138 | 136 | 140 | p < 0.0001 |
|  | Treated = 48 | 141 | 144 | 138 |  |
|  |  | 2% | 6%* | −1% |  |
| Riluzole-1 | Control = 20 | 132 | 133 | 130 | Not Significant |
|  | Treated = 20 | 134 | 131 | 138 |  |
|  |  | 2% | −1.5% | 6% |  |
| Riluzole-2 | Control = 14 | 133 | 129 | 136 | Not Significant |
|  | Treated = 15 | 136 | 136 | 136 |  |
|  |  | 2% | 5% | None |  |
| Combined Riluzole (100% Litter matched) | Control = 33 | 132 | 132 | 133 | Not Significant |
|  | Treated = 33 | 135 | 133 | 137 |  |
|  |  | 2% | 1% | 3% |  |

@% effect = {(mean treated-mean control)/mean control}*100
**p = 0.03 Significant Treatment gender interaction (Cox proportional hazard analysis with frailty term as gender and litter)
*p = 0.06 (Cox proportional hazard analysis with frailty term as litter.
¶Mixed piece wise linear analysis for treatment gender interaction with frailty term as gender and litter.

TABLE 2

Summarized data on control untreated animals from ALS-TDF Ritonavir ® and Riluzole studies

| Controls | Males (Days) | Females (Days) | Percentage gender effect@ |
|---|---|---|---|
| Ritonavir-1 | 135 | 142 | 5% |
| Ritonavir-2 | 142 | 136 | −4% |
| Ritonavir-3 | 130 | 141 | 9% |
| Combined Ritonavir | 136 | 140 | 3% |
| Riluzole-1 | 133 | 130 | −2% |
| Riluzole-2 | 129 | 136 | 5% |
| Combined Riluzole | 132 | 133 | 1% |
| Cumulative N = 575 | 130 | 135 | 4%** |

@Percentage effect = {(mean female − mean male)/mean male}*100
**p < 0.0001 Significant gender interaction (Cox proportional hazard analysis with frailty term as litter)

In summary, Ritonavir® treatment results in a reproducible slowing of disease progression (neurological score) and prolongation of survival in the SOD1 G93A mouse model of ALS. Ritonavir® degree of efficacy exceeds (neurological score) or equals (survival) exceeds that of riluzole (Rilutek®), the only drug both approved for use in ALS and active in this model (i.e. the model's positive control drug). Accordingly, Ritonavir® provides an alternative method for modulating proteasome activity in cells associated with ALS, such that the modulation of the proteasome activity improves survival in a murine model of ALS, as well as the improves neurological score in animals treated with Ritonavir® From this effort, three separate studies employing very similar dosing paradigms all support the conclusion that Ritonavir® is more active than the positive control drug in this model riluzole (Rilutek®). In conclusion, the efficacy demonstrated by Ritonavir® in the SOD1 mouse model of ALS, together with good toleration in large-scale trials in AIDS patients, makes it a good candidate for clinical study in ALS patients.

Example 3

Modulation of ALS in an ALS Patient

The method of the invention can be used to administer Ritonavir® to a patient afflicted with a neurodegenerative disease, such as ALS at a daily dosage of about 200 mg/day to about 1200 mg/day for about 3-6 months. The effects of Ritonavir® administration can be monitored by examining the alleviation of the disease, a decrease in progression of the disease, or an amelioration of the symptoms of ALS in the patient. The therapeutic effects of Ritonavir® in ALS can be assessed, for example, by monitoring an improvement in muscle activity, or reflexive activity of the patient, such as the improved ability of the patient to swallow or move limbs. Alternatively, the therapeutic effects of Ritonavir® can be determined by improving the patient's survival.

The results from an ALS patient who was given Ritonavir® at a daily dosage of 400 mg/day for about nine months demonstrated that since taking Ritonavir®, the patient experienced beneficial effects. The beneficial therapeutic effects of Ritonavir® were experienced after three weeks of Ritonavir® administration, and resulted in ameliorating the effects of ALS, slowing progression of the disease, and improving survival of the patient.

(a) Initial Status Prior to Treatment with Ritonavir®

The patient was on ventilator and non-ambulatory. The patient was paralyzed below the waist except the neck region, and communicated with head movement using Morse code based computer keys. The patient was also unable to swallow and hence feeding was done using a stomach tube. The biceps and forearms of the patient were paralyzed for several years.

The patient speculated that since the left side deteriorated about one and a half years after the right side, that left side was significantly less damaged than the right side.

(b) Assessment of Muscle Activity after treatment with Ritonavir®

After administering Ritonavir® for nine months, the patient underwent neurological examination. The results from the neurological examination showed that the patient's diaphragm has gained enough strength to dislodge a tracheostomy cuff when sneezing, demonstrating that the muscles in the chest had gained strength. The patient's tongue was stronger, and the patient was also able to swallow after three years of being unable to swallow, as demonstrated by the patient regularly consuming soup by mouth.

The pectoral muscles also gained significant strength, and the complex of trapezius, shoulders and triceps were shown to be stronger. The patient also exhibited an improvement in the ability to make facial expressions, as well as an improvement in neck muscles, demonstrating that these muscles were significantly stronger than before the treatment with Ritonavir®.

Moreover, some muscles that had been paralyzed for years were again under conscious control and showed electrical nerve activity after treatment with Ritonavir®. These include large muscle groups, such as the pectoral muscles, gluteal muscles, buttocks, hamstrings, biceps, left side of the quadriceps and some muscles in the calf and the little finger of the left hand. The patient was able to flex both buttocks and left hamstring.

In summary, this data demonstrates that Ritonaviro improves the symptoms of ALS, slows progression of the disease, and prolongs the survival of the patient, and helped improve the quality of life of the patient.

What is claimed is:

1. A method of assessing whether a subject is afflicted with a neurodegenerative disease selected from the group consisting of Amyotrophic Lateral Sclerosis (ALS), multiple sclerosis, Huntington's disease, Parkinson's disease, prion associated disease, spinal muscular atrophy, spinal cerebellar ataxia, and spinal cord injury, the method comprising, comparing:
    the level of proteasome activity in a test sample from a subject, by measuring the expression levels in the test sample of at least one proteasome subunit selected from the group consisting of LMP-2, LMP-7 and MECL-1, and
    a normal level of proteasome activity for said at least one proteasome subunit,
    wherein a significant difference between the level of proteasome activity in the test sample and the normal level is an indication that the subject is afflicted with a neurodegenerative disease.

2. The method of claim 1, wherein the proteasome subunit is LMP-2.

3. The method of claim 1, wherein the proteasome subunit is LMP-7.

4. The method of claim 1, wherein the proteasome subunit is MECL-1.

5. A method of assessing whether a subject is afflicted with Amyotrophic Lateral Sclerosis (ALS), the method comprising,
    measuring the expression level of at least one proteasome subunit selected from the group consisting of LMP-2, LMP-7 and MECL-1 in a test sample from a subject, and
    comparing the measured level with a normal level wherein a significant difference between the measured level and the normal level is an indication that the subject is afflicted with a Amyotrophic Lateral Sclerosis.

6. The method of claim 5, wherein the proteasome subunit is LMP-2.

7. The method of claim 5, wherein the proteasome subunit is LMP-7.

8. The method of claim 5, wherein the proteasome subunit is MECL-1.

9. The method of claim 5, wherein elevated levels of LMP-2, LMP-7 or MECL-1 in a test sample indicates that the subject is afflicted with amyotrophic Lateral Sclerosis (ALS).

10. A method of assessing whether a subject is at risk for developing Amyotrophic Lateral Sclerosis (ALS), the method comprising,
    measuring the expression level of at least one proteasome subunit in a test sample from a subject, and
    comparing the measured level with a normal level, wherein a significant difference between the measured level and the normal level is an indication that the subject is at risk for developing ALS.

11. The method of claim 10, wherein the proteasome subunit is selected from the group consisting of LMP-2, LMP-7 and MECL-1.

12. The method of claim 10, wherein elevated levels of at least one of LMP-2, LMP-7 or MECL-1 in a test sample indicates that the subject is at risk for developing ALS.

* * * * *